(12) United States Patent
Ohkawa et al.

(10) Patent No.: US 11,474,600 B2
(45) Date of Patent: Oct. 18, 2022

(54) EYEBALL DETECTION UNIT AND IMAGE DISPLAY APPARATUS

(71) Applicant: SONY CORPORATION, Tokyo (JP)

(72) Inventors: Shingo Ohkawa, Tokyo (JP); Ryo Ogawa, Tokyo (JP); Susumu Seino, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 17/250,159

(22) PCT Filed: May 24, 2019

(86) PCT No.: PCT/JP2019/020646
§ 371 (c)(1),
(2) Date: Dec. 7, 2020

(87) PCT Pub. No.: WO2019/239849
PCT Pub. Date: Dec. 19, 2019

(65) Prior Publication Data
US 2021/0325961 A1    Oct. 21, 2021

(30) Foreign Application Priority Data

Jun. 14, 2018  (JP) .............................. JP2018-113779

(51) Int. Cl.
| | | |
|---|---|---|
| *G06F 3/01* | (2006.01) | |
| *G06T 7/73* | (2017.01) | |
| *G06V 40/19* | (2022.01) | |

(52) U.S. Cl.
CPC .............. *G06F 3/013* (2013.01); *G06T 7/74* (2017.01); *G06V 40/19* (2022.01); *G06T 2207/30201* (2013.01)

(58) Field of Classification Search
CPC ............... G01B 11/00; G02B 27/0093; G02B 27/0172; G02B 2027/0138;
(Continued)

(56) References Cited

U.S. PATENT DOCUMENTS

| | | |
|---|---|---|
| 5,335,035 A | 8/1994 | Maeda |
| 8,824,779 B1 * | 9/2014 | Smyth ....................... G06T 7/73 |
| | | 382/117 |

(Continued)

FOREIGN PATENT DOCUMENTS

| | | |
|---|---|---|
| CN | 102670173 A | 9/2012 |
| CN | 103565403 A | 2/2014 |

(Continued)

OTHER PUBLICATIONS

International Search Report and Written Opinion of PCT Application No. PCT/JP2019/020646, dated Jul. 9, 2019, 06 pages of ISRWO.

(Continued)

*Primary Examiner* — Nelson M Rosario
(74) *Attorney, Agent, or Firm* — Chip Law Group

(57) ABSTRACT

An eyeball detection unit of the present disclosure includes an irradiator that projects substantially parallel illumination light toward a cornea of an eyeball, a detector that detects light intensity of reflected light from the cornea, and a detection controller that identifies a centroid offset in an angular direction of the light intensity of the reflected light from the cornea with respect to a reference optical axis on the basis of a detected value by the detector, and thereafter calculates a positional offset of a cornea position with respect to the reference optical axis.

9 Claims, 28 Drawing Sheets

(58) Field of Classification Search
CPC ... G02B 2027/0187; G06F 3/013; G06T 7/74; G06T 2207/30201; G06V 40/19; A61B 3/113

See application file for complete search history.

(56) References Cited

U.S. PATENT DOCUMENTS

| | | | |
|---|---|---|---|
| 10,928,894 B2* | 2/2021 | Bitauld | G02B 27/0172 |
| 2018/0239423 A1* | 8/2018 | Mardanbegi | A61B 3/113 |

FOREIGN PATENT DOCUMENTS

| | | |
|---|---|---|
| JP | 05-232373 A | 9/1993 |
| JP | H05232373 A | 9/1993 |
| JP | 05-344954 A | 12/1993 |
| JP | H05344954 A | 12/1993 |
| JP | 06-054807 A | 3/1994 |
| JP | 06-230482 A | 8/1994 |
| JP | H06230482 A | 8/1994 |
| JP | 09-325260 A | 12/1997 |
| JP | 2005-287782 A | 10/2005 |
| JP | 2006-058505 A | 3/2006 |
| JP | 2005287782 A | 10/2006 |
| JP | 2014-188322 A | 10/2014 |
| JP | 2018-113779 A | 7/2018 |
| WO | 2016124668 A1 | 8/2016 |

OTHER PUBLICATIONS

First Office Action for Chinese Patent Application Serial No. 201980038086.8 dated Jun. 15, 2022.

\* cited by examiner

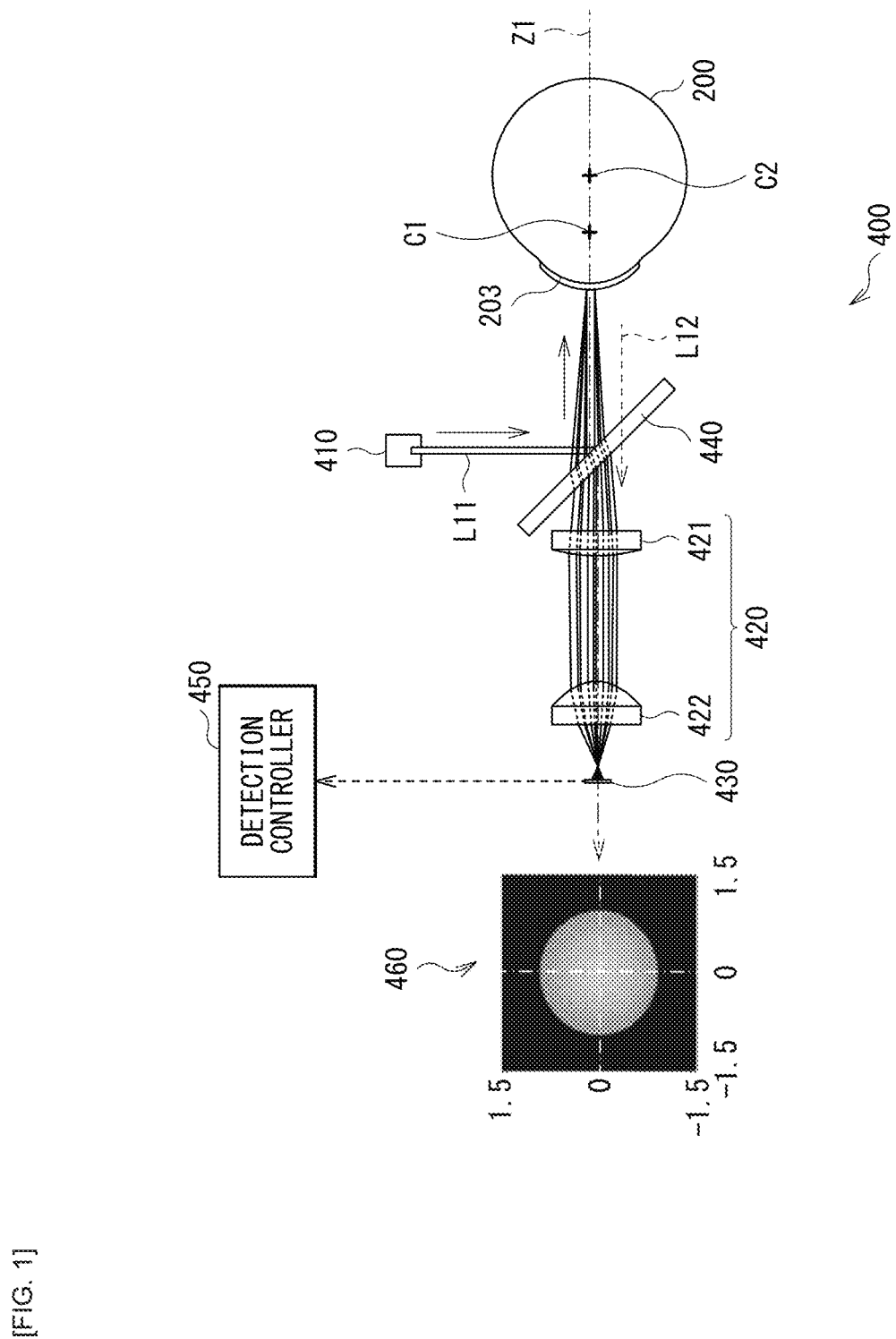
[FIG. 1]

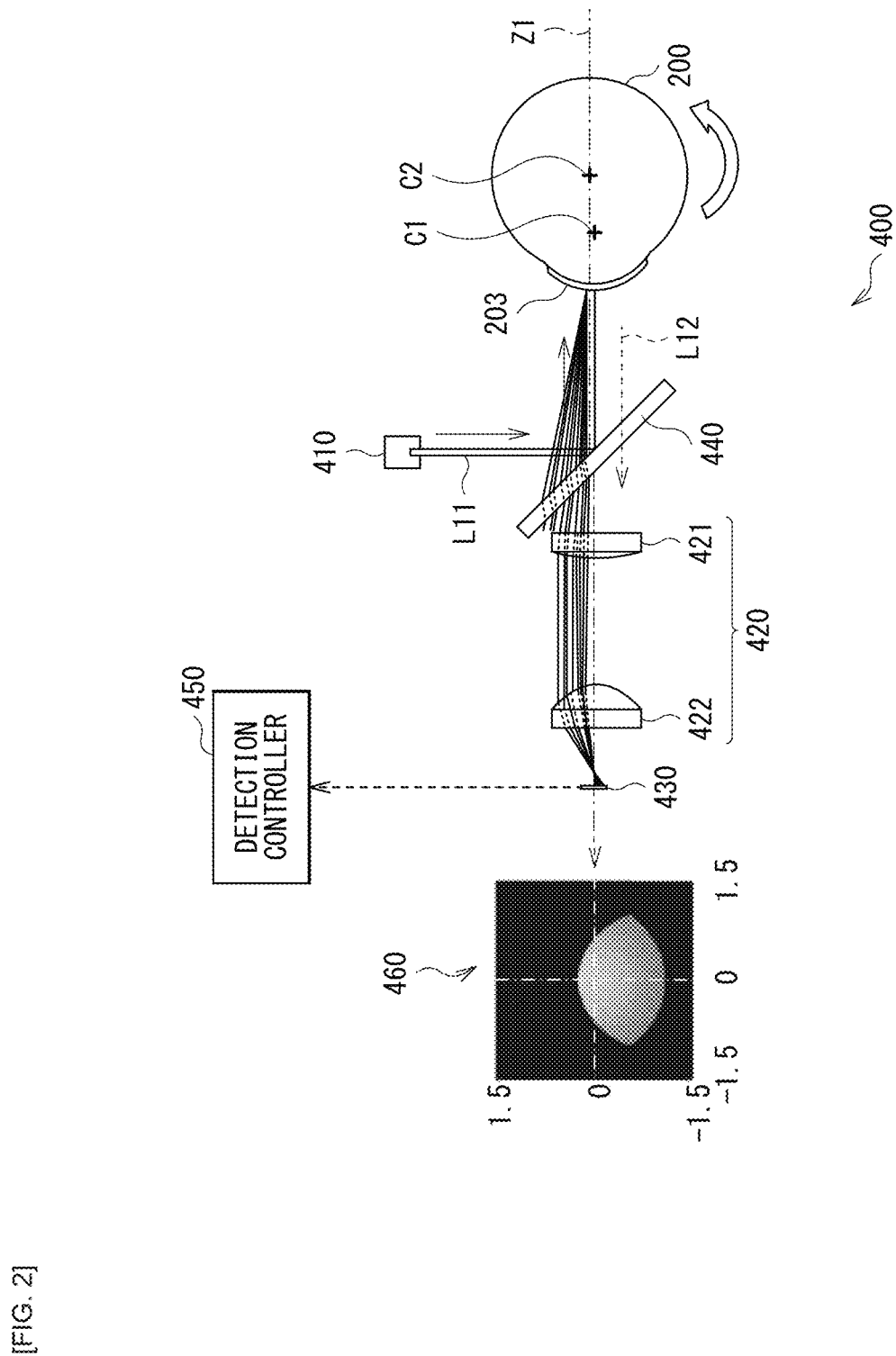
[FIG. 2]

[FIG. 3]
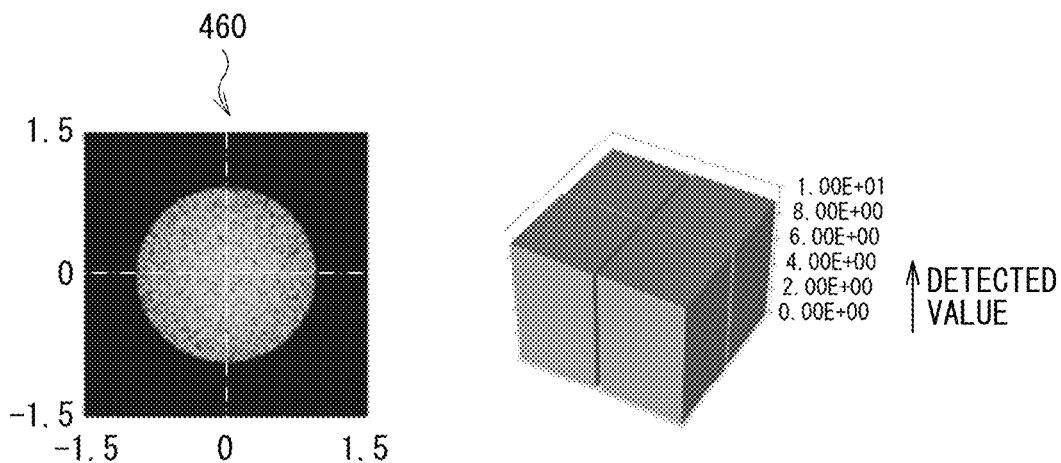
[FIG. 4]
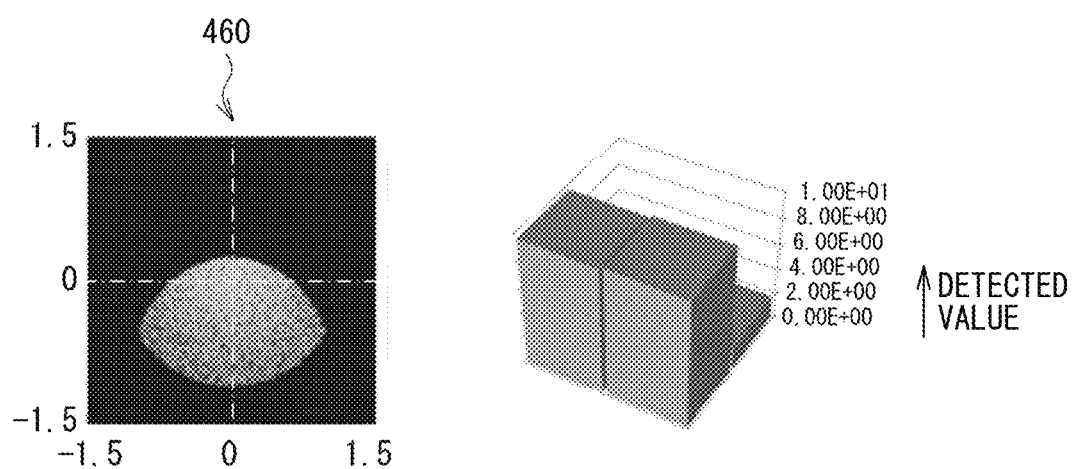

[FIG. 5]
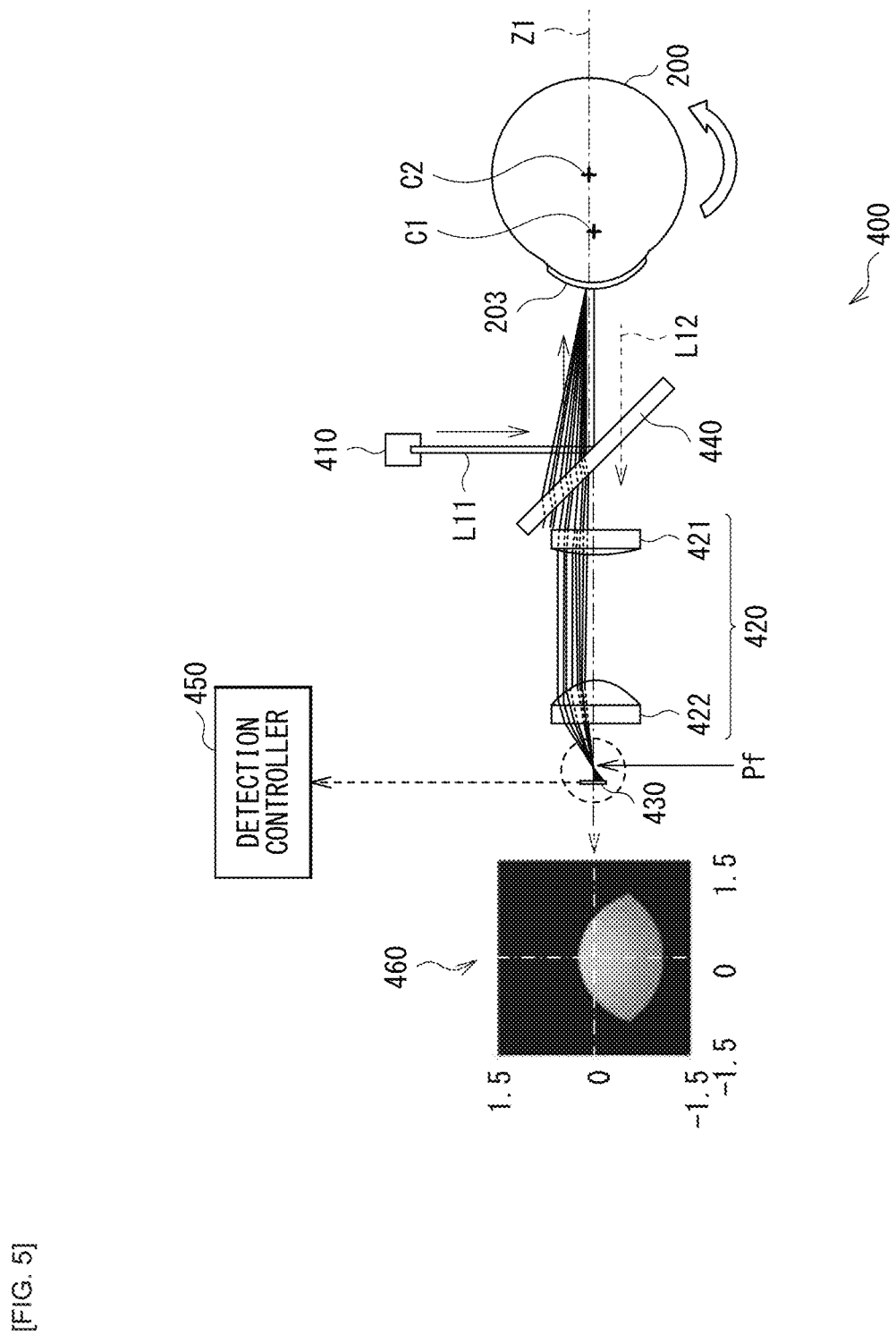

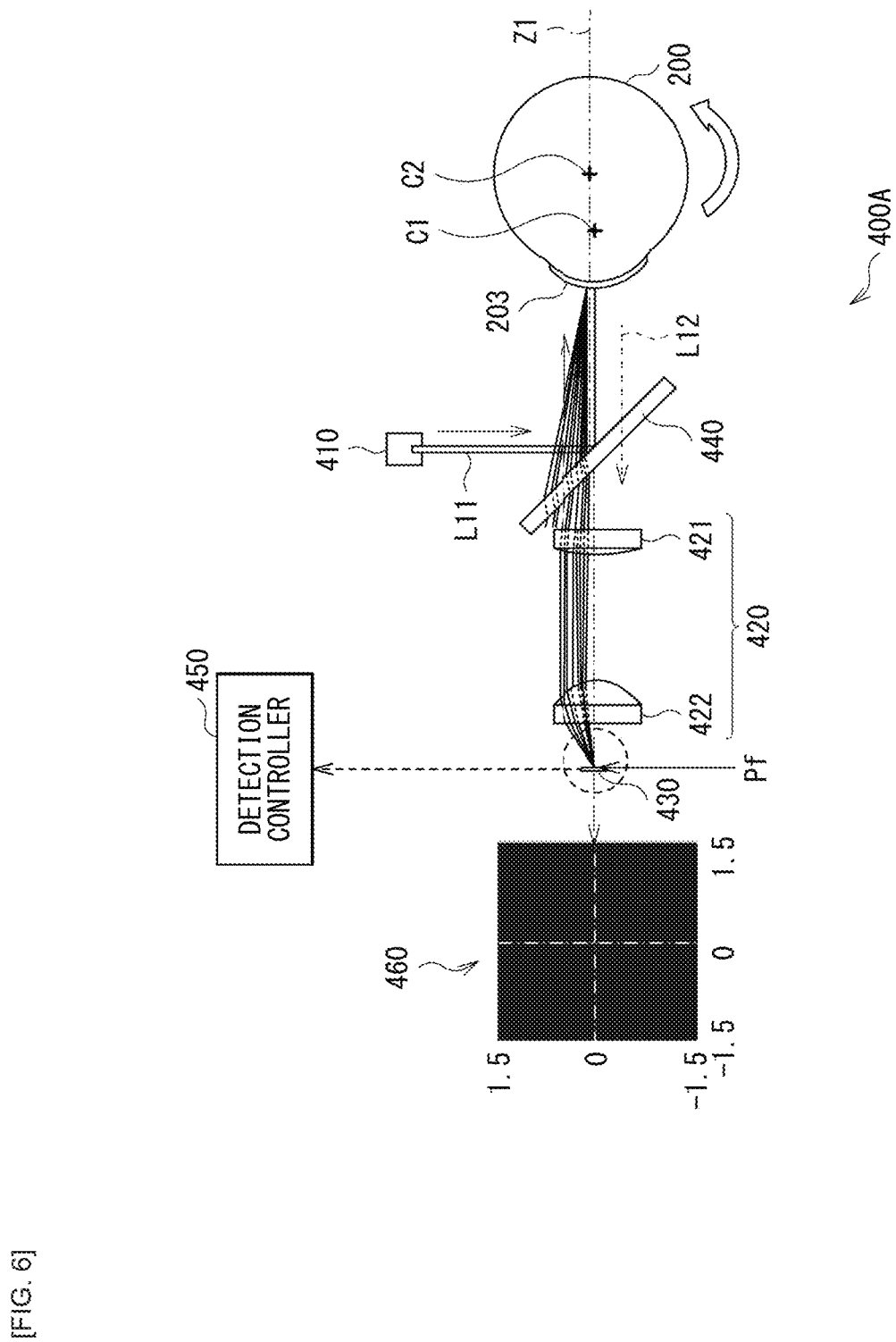

[FIG. 7]
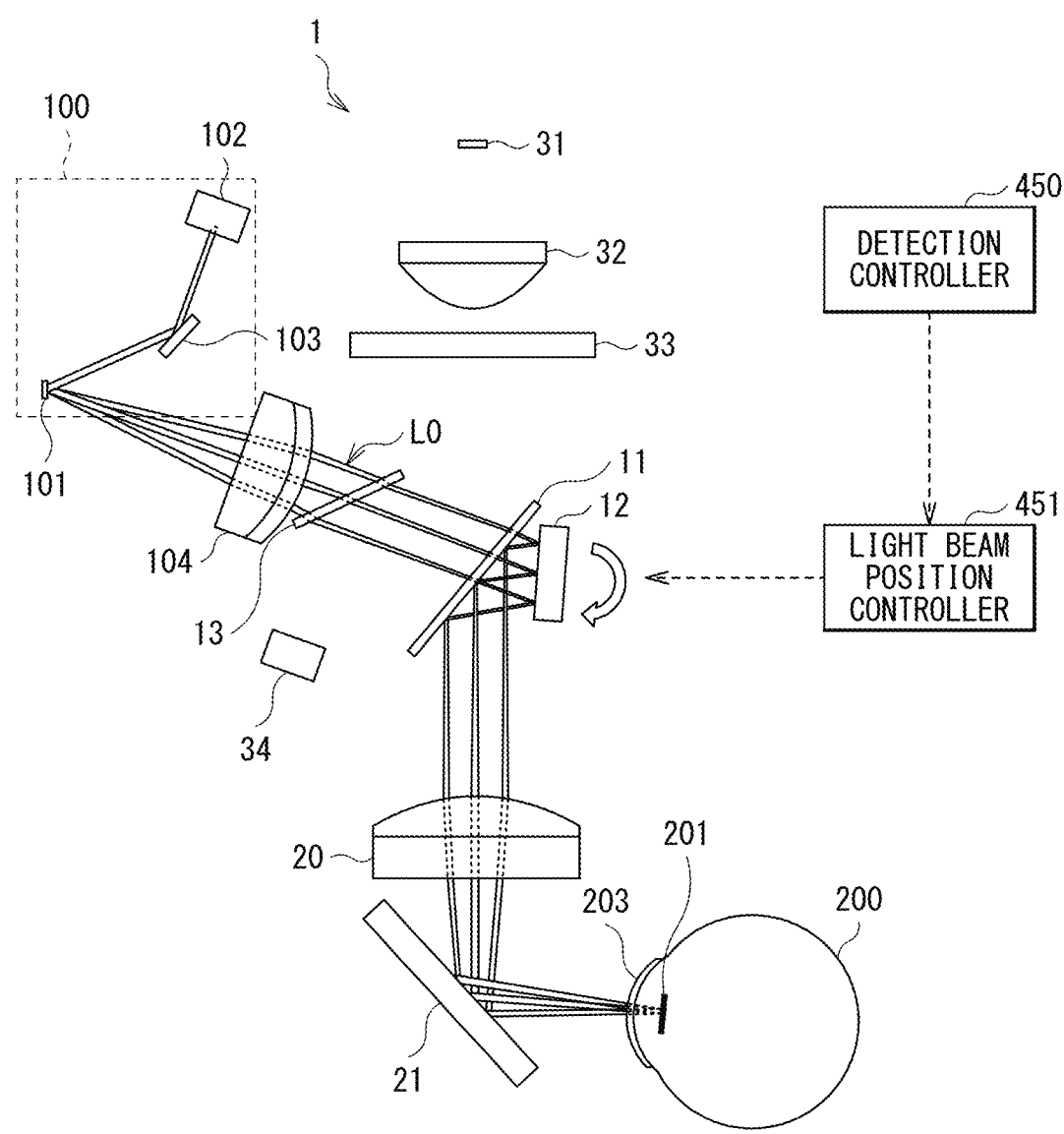

[FIG. 8]
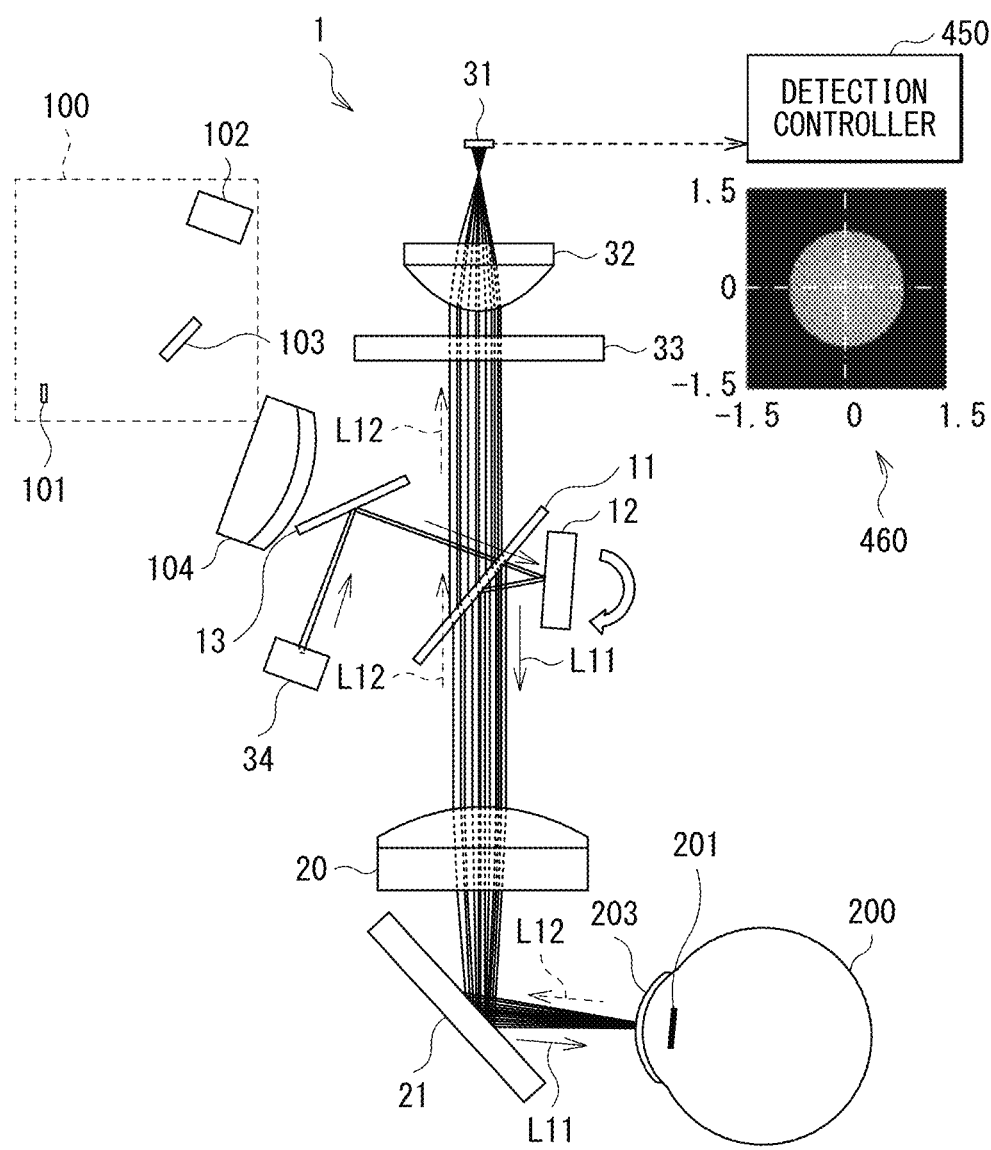

[FIG. 9]
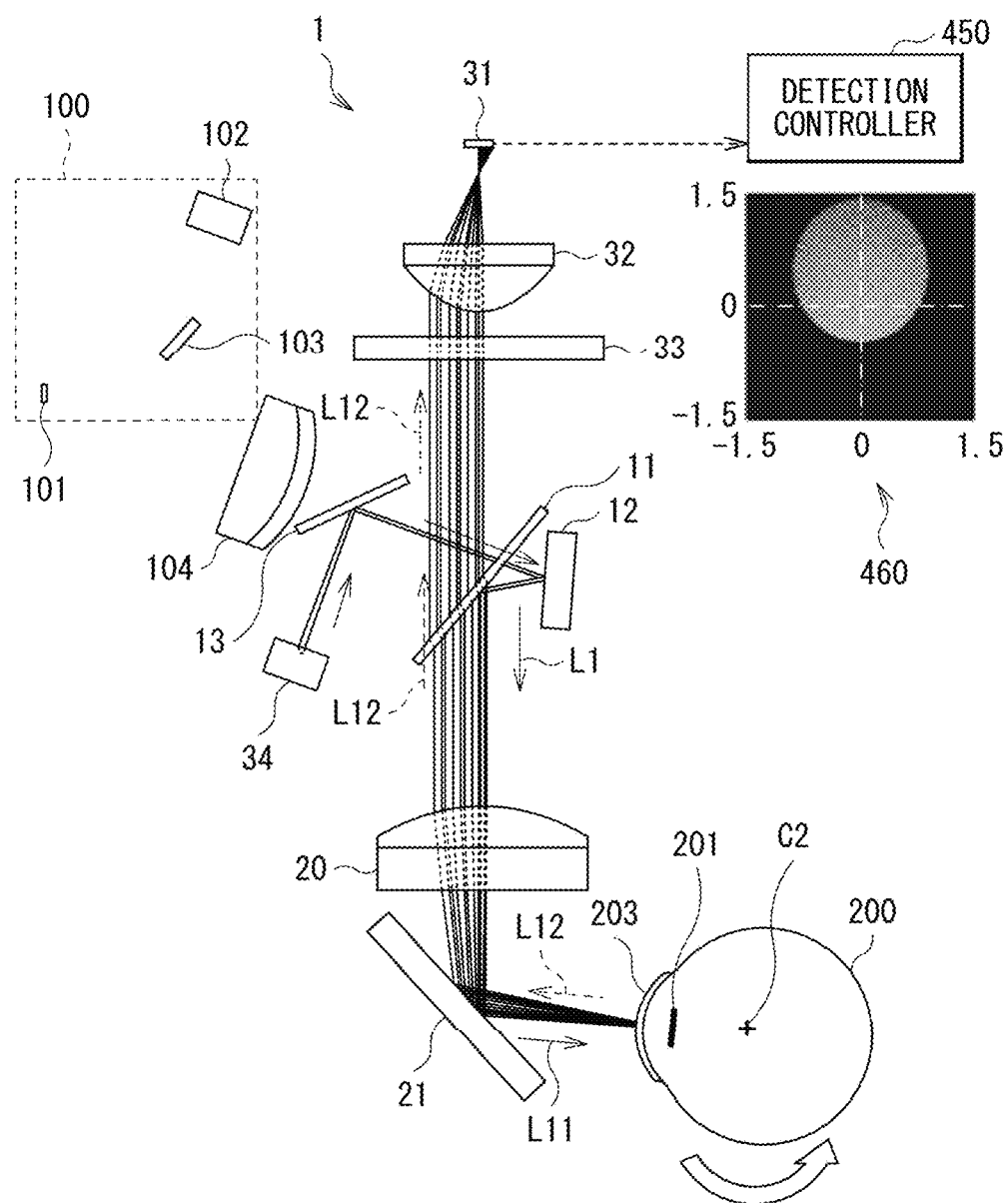

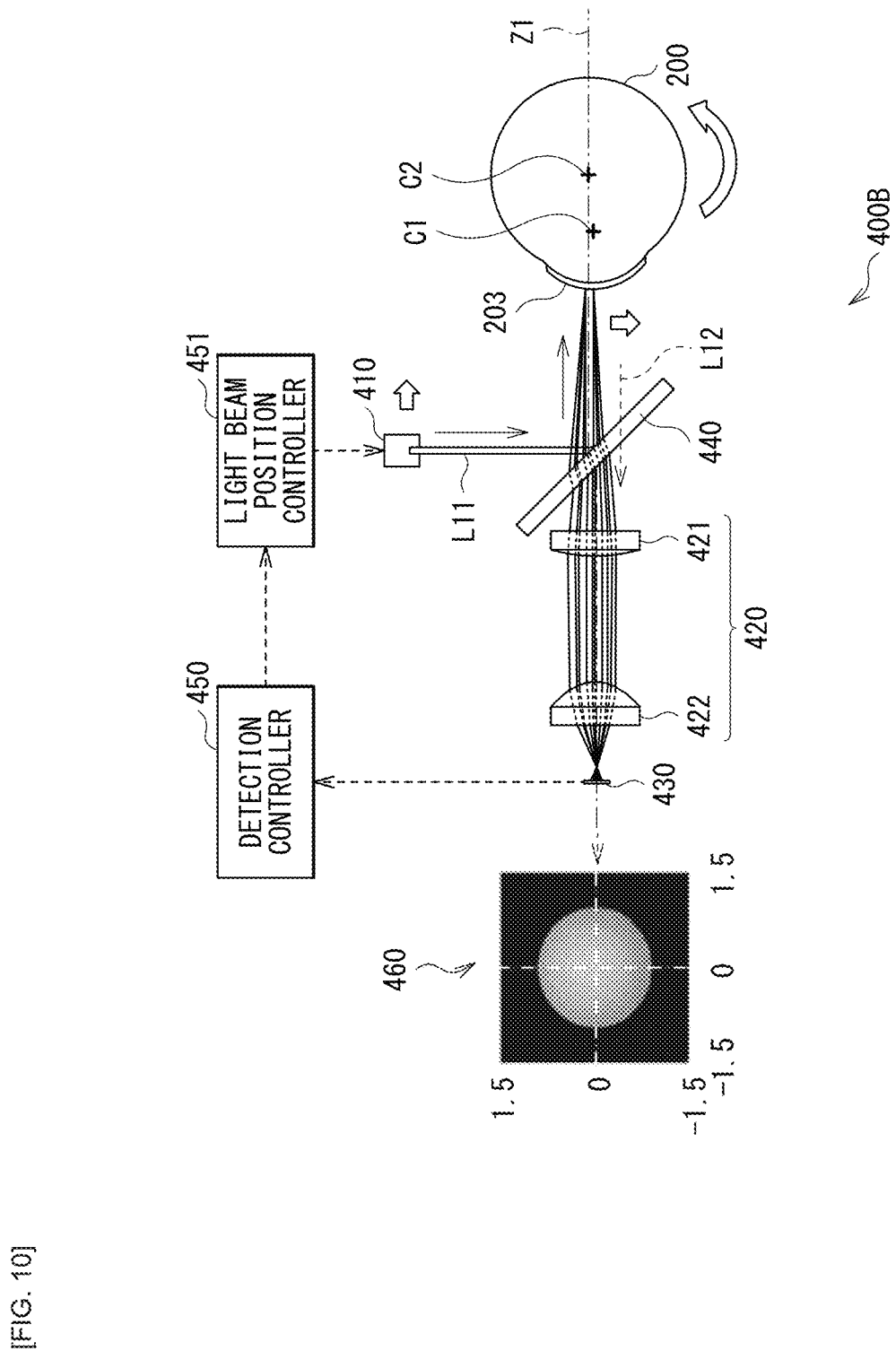
[FIG. 10]

[FIG. 11]
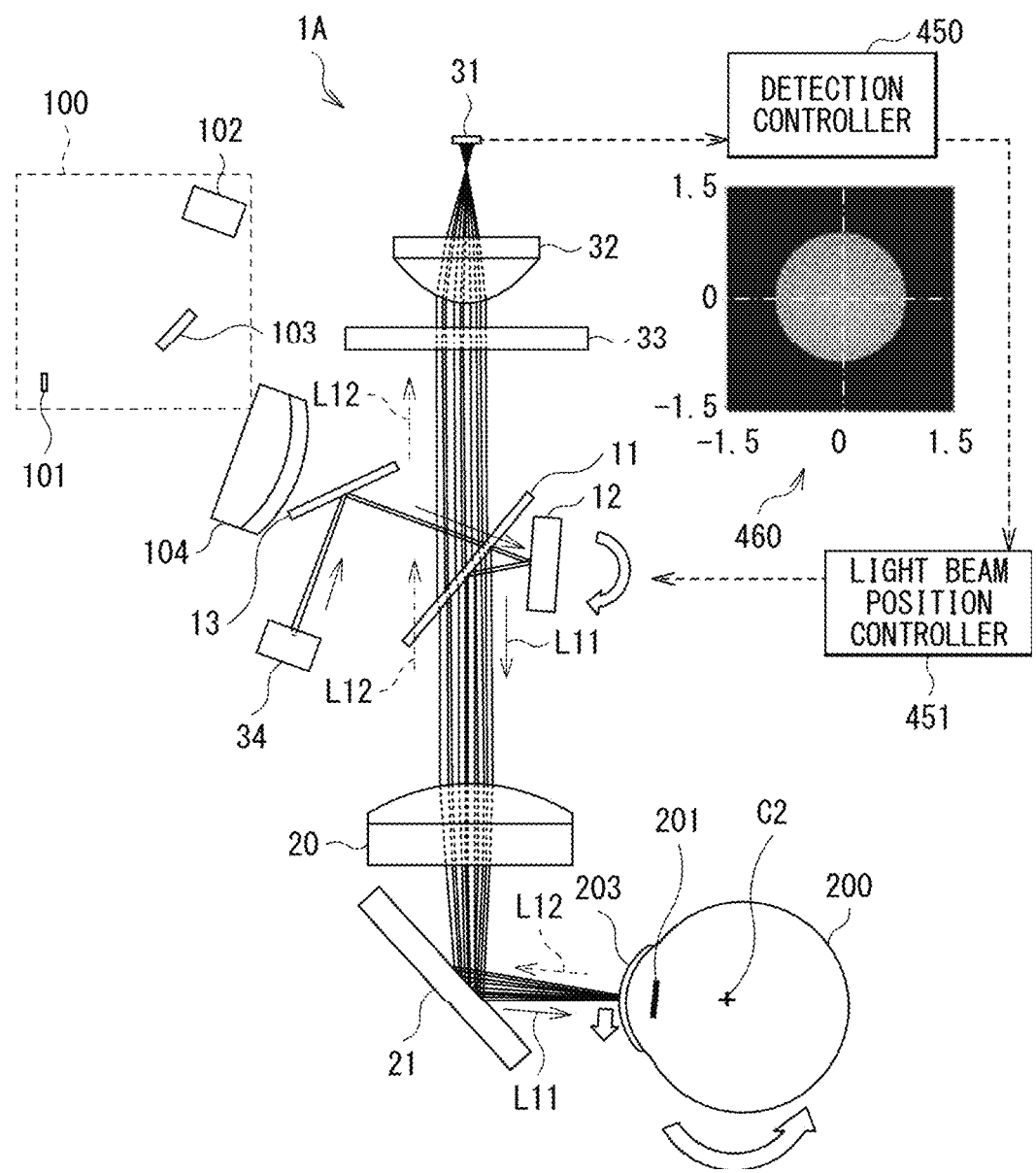

[FIG. 12]
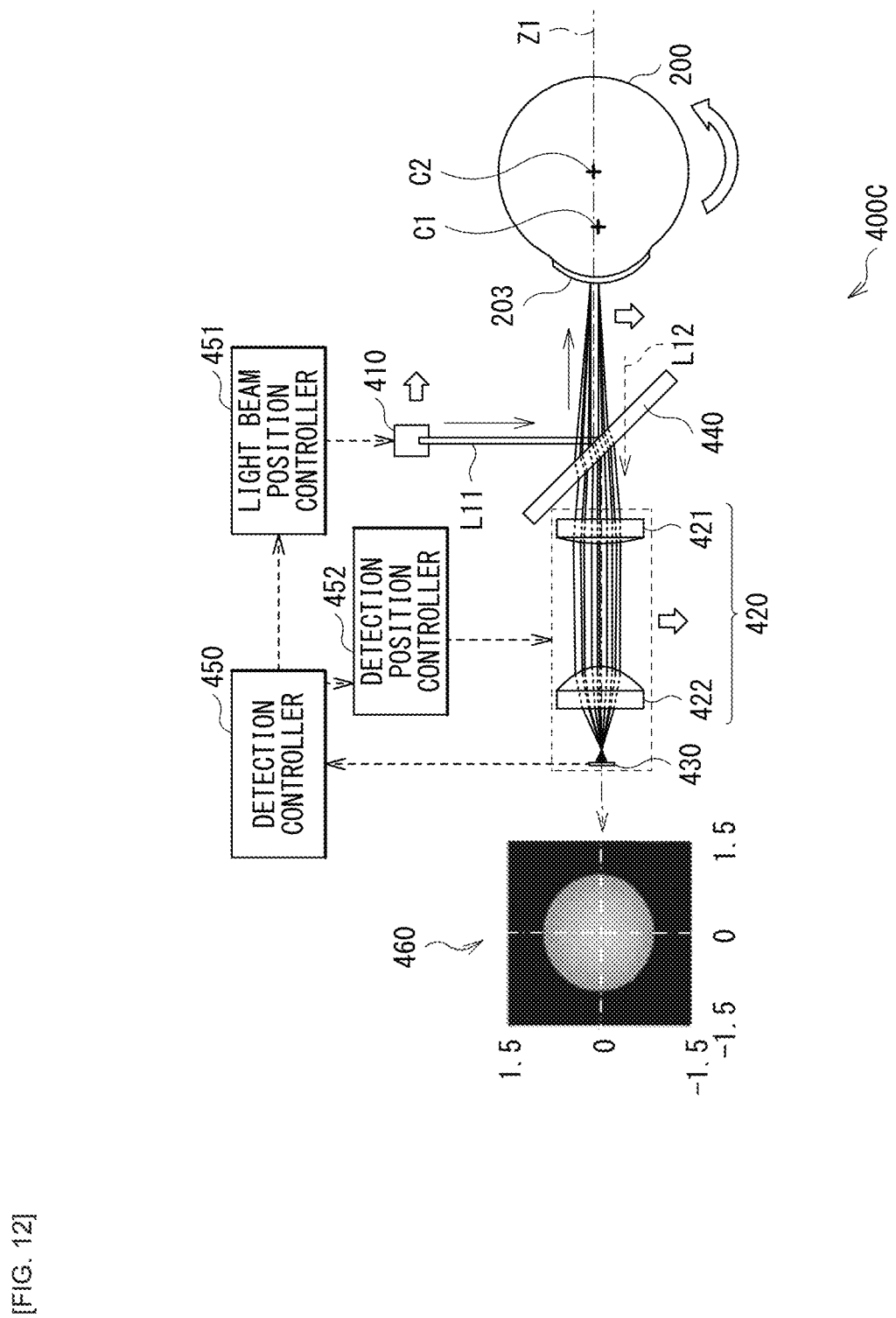

[FIG. 13]
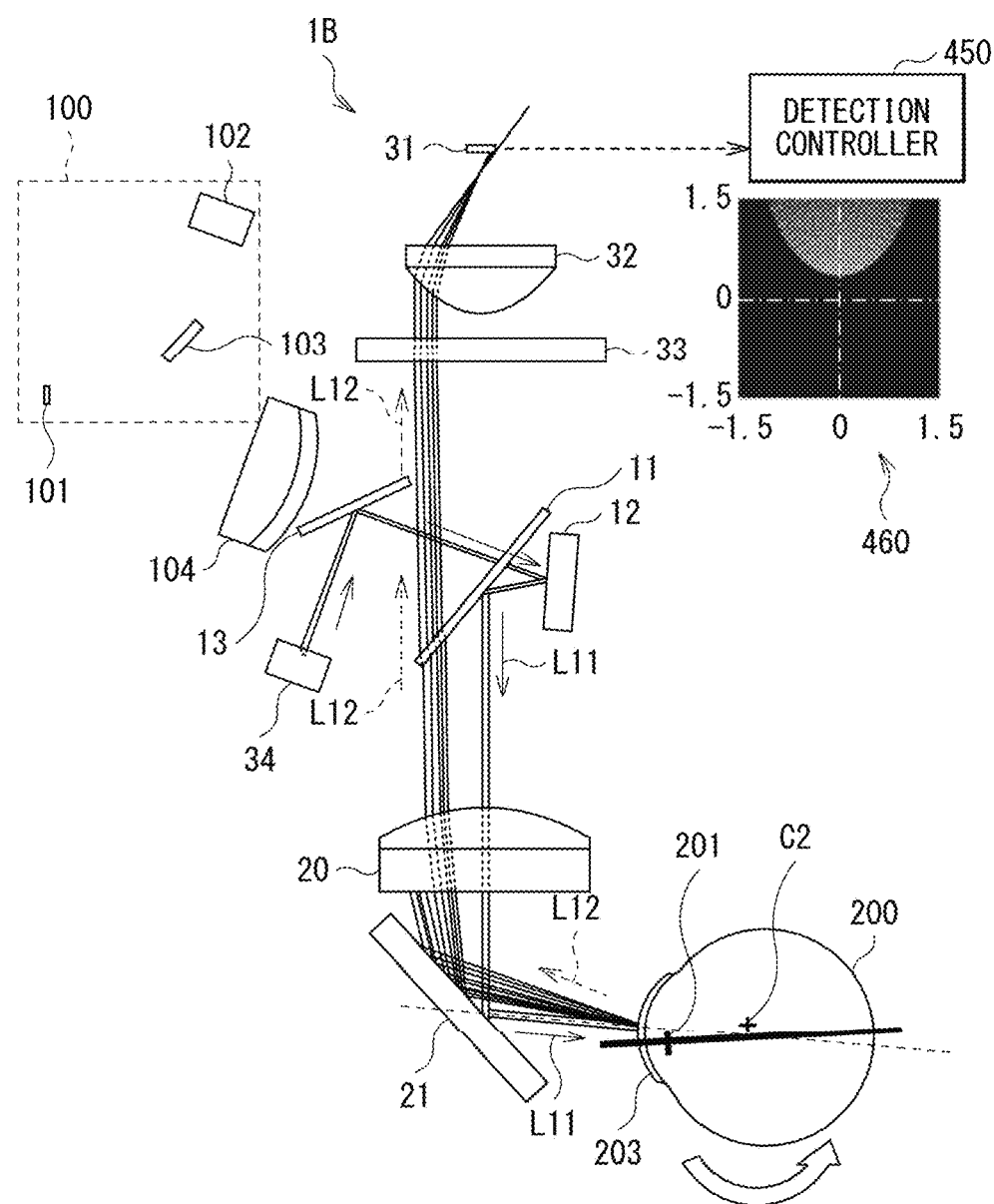

[FIG. 14]
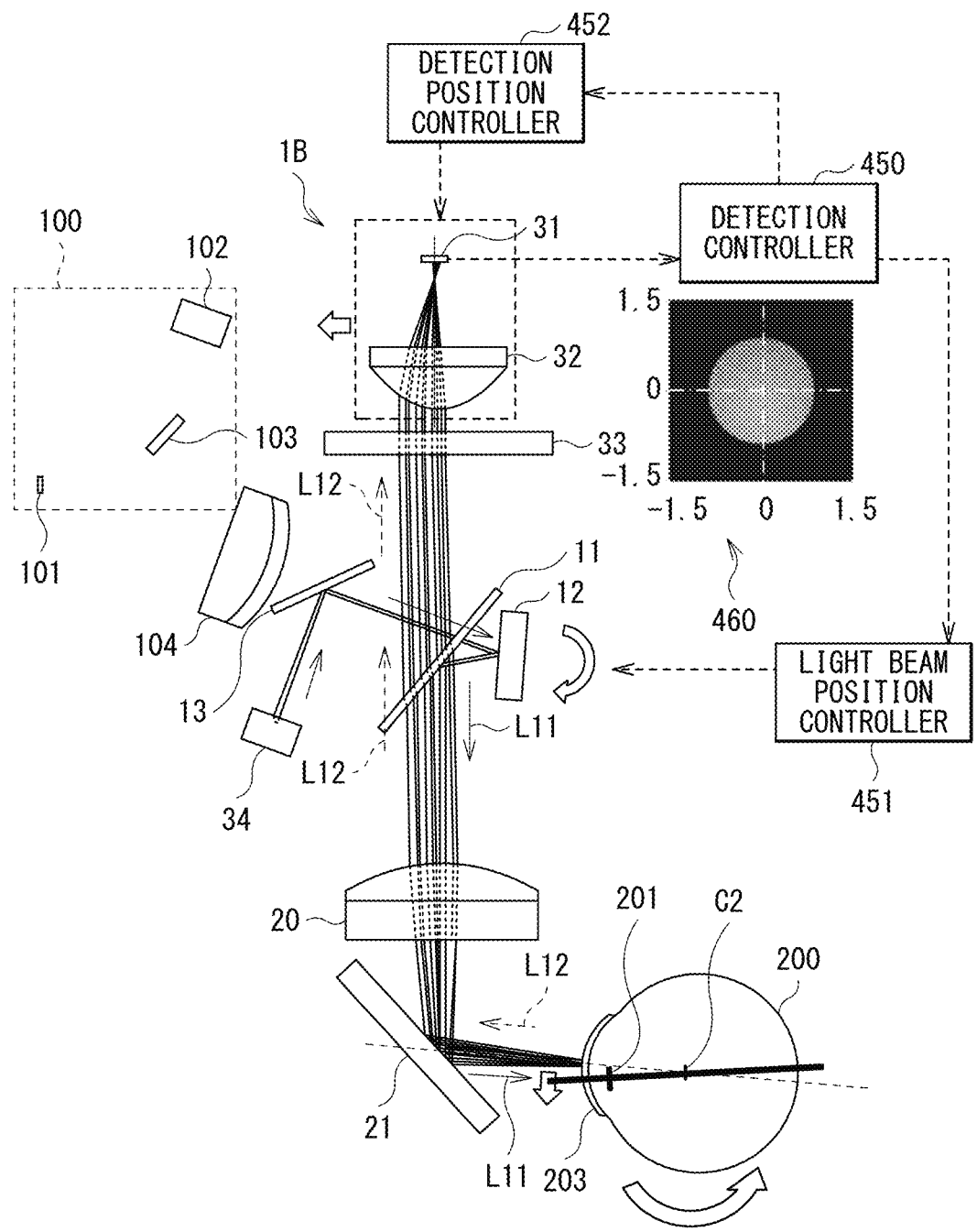

[FIG. 15]

| PROJECTION POSITION OF ILLUMINATION LIGHT (AMOUNT OF MOVEMENT) | POSITIONAL OFFSET OF CORNEA POSITION | | | |
|---|---|---|---|---|
| | EYEBALL ROTATION OF 0° (POSITIONAL OFFSET OF 0 mm) | EYEBALL ROTATION OF 5° (POSITIONAL OFFSET OF 0.8 mm) | EYEBALL ROTATION OF 10° (POSITIONAL OFFSET OF 1.6 mm) | EYEBALL ROTATION OF 15° (POSITIONAL OFFSET OF 2.4 mm) |
| 0 mm (OPTIMUM POSITION FOR EYEBALL ROTATION OF 0°) | 1.65E-02  1.71E-02<br>1.85E-02  1.74E-02 | 2.33E-02  1.19E-02<br>2.53E-02  9.82E-03 | 1.83E-02  4.56E-03<br>1.42E-02  4.20E-03 | 2.61E-03  0.00E+00<br>3.01E-03  6.81E-04 |
| 0.8 mm TO RIGHT (OPTIMUM POSITION FOR EYEBALL ROTATION OF 5°) | 1.78E-02  1.15E-02<br>1.64E-02  1.31E-02 | 2.25E-02  1.98E-02<br>2.37E-02  8.80E-03 | 2.67E-02  3.31E-03<br>2.64E-02  4.77E-03 | 2.98E-02  0.00E+00<br>3.03E-02  7.39E-04 |
| 1.6 mm TO RIGHT (OPTIMUM POSITION FOR EYEBALL ROTATION OF 10°) | 3.65E-03  3.02E-03<br>3.85E-03  2.95E-03 | 1.39E-02  1.91E-03<br>1.11E-02  1.99E-03 | 2.93E-02  3.70E-03<br>2.88E-02  3.02E-03 | 3.13E-02  4.79E-04<br>3.47E-02  9.33E-04 |
| 2.4 mm TO RIGHT (OPTIMUM POSITION FOR EYEBALL ROTATION OF 10°) | 1.83E-03  1.36E-03<br>1.68E-03  1.79E-03 | 5.67E-03  1.82E-03<br>5.05E-03  1.66E-03 | 7.28E-03  5.84E-04<br>6.95E-03  3.62E-04 | 1.96E-02  0.00E+00<br>2.26E-02  2.76E-04 |

OPTIMUM VALUE OF RELATIONSHIP BETWEEN POSITIONAL OFFSET AND PROJECTION POSITION

[FIG. 16]
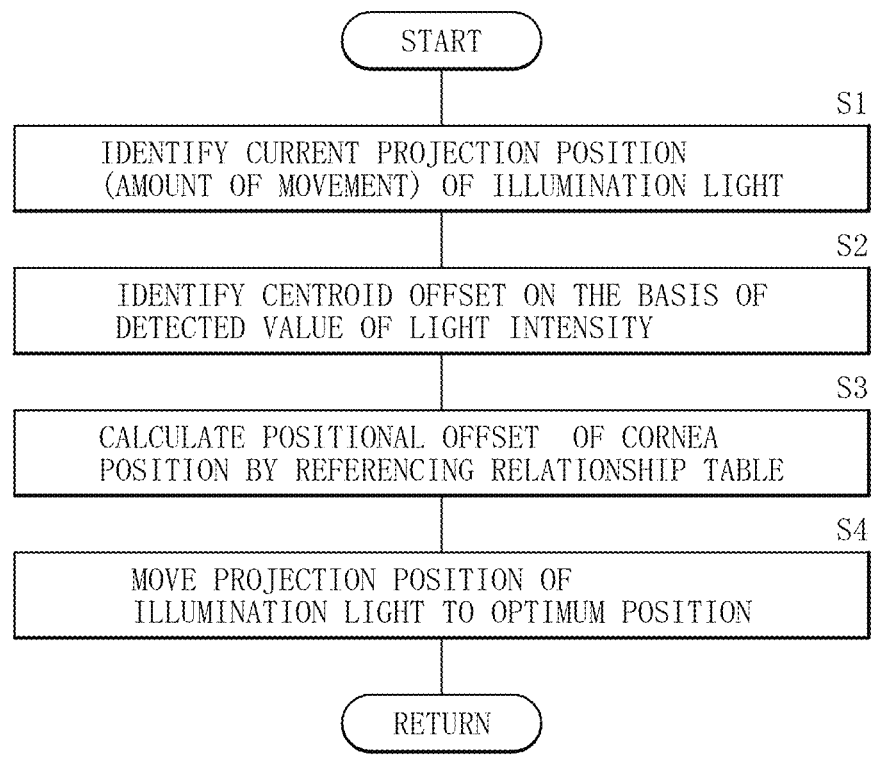

[FIG. 17]
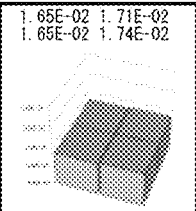

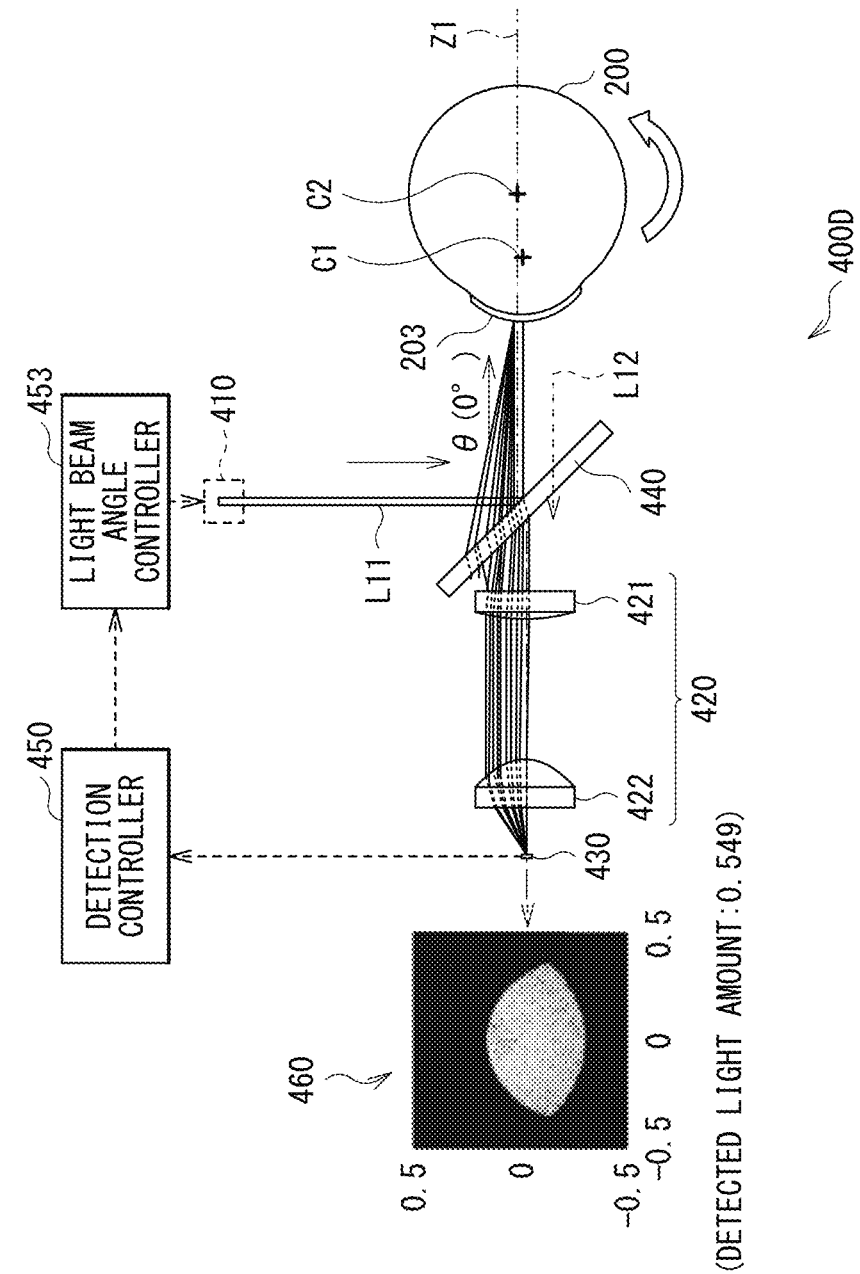
[FIG. 18]

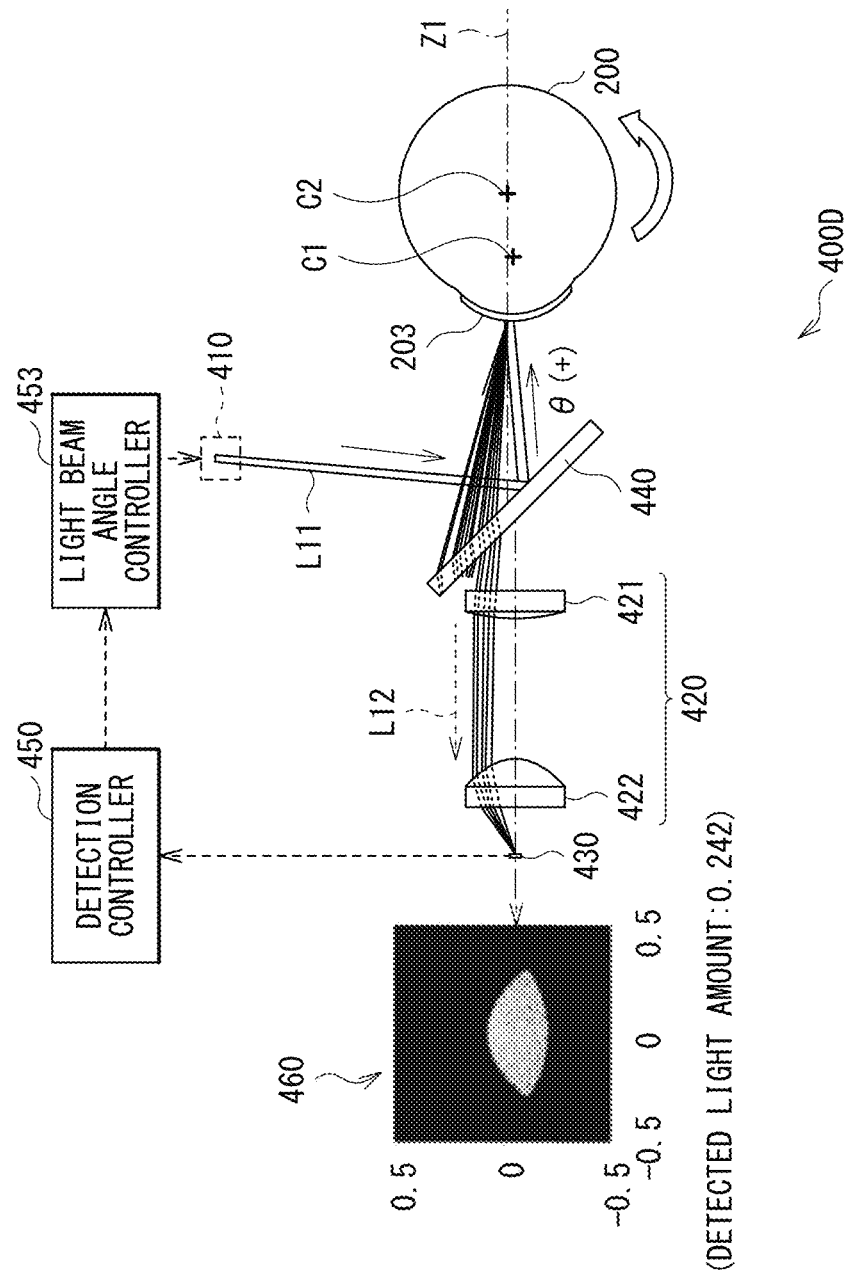

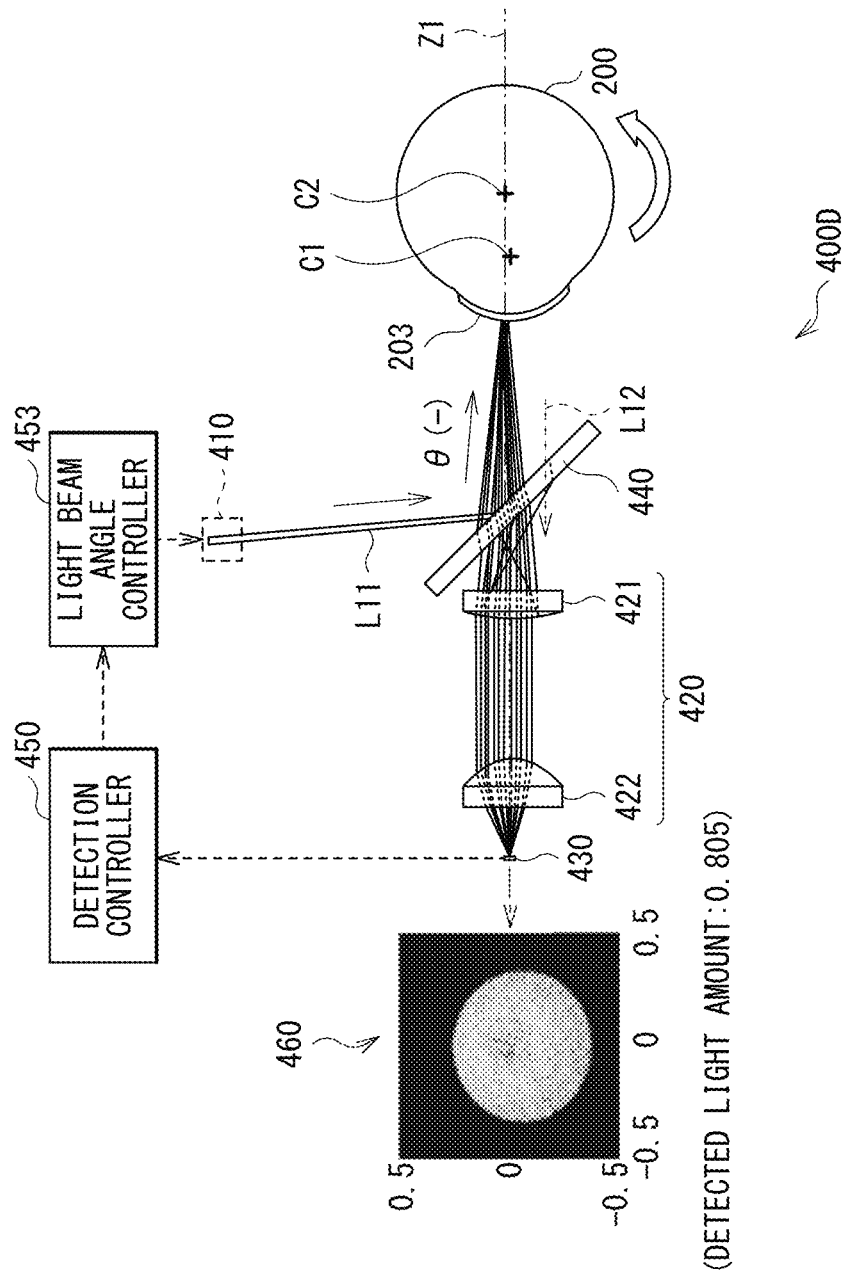
[FIG. 20]

[FIG. 21]
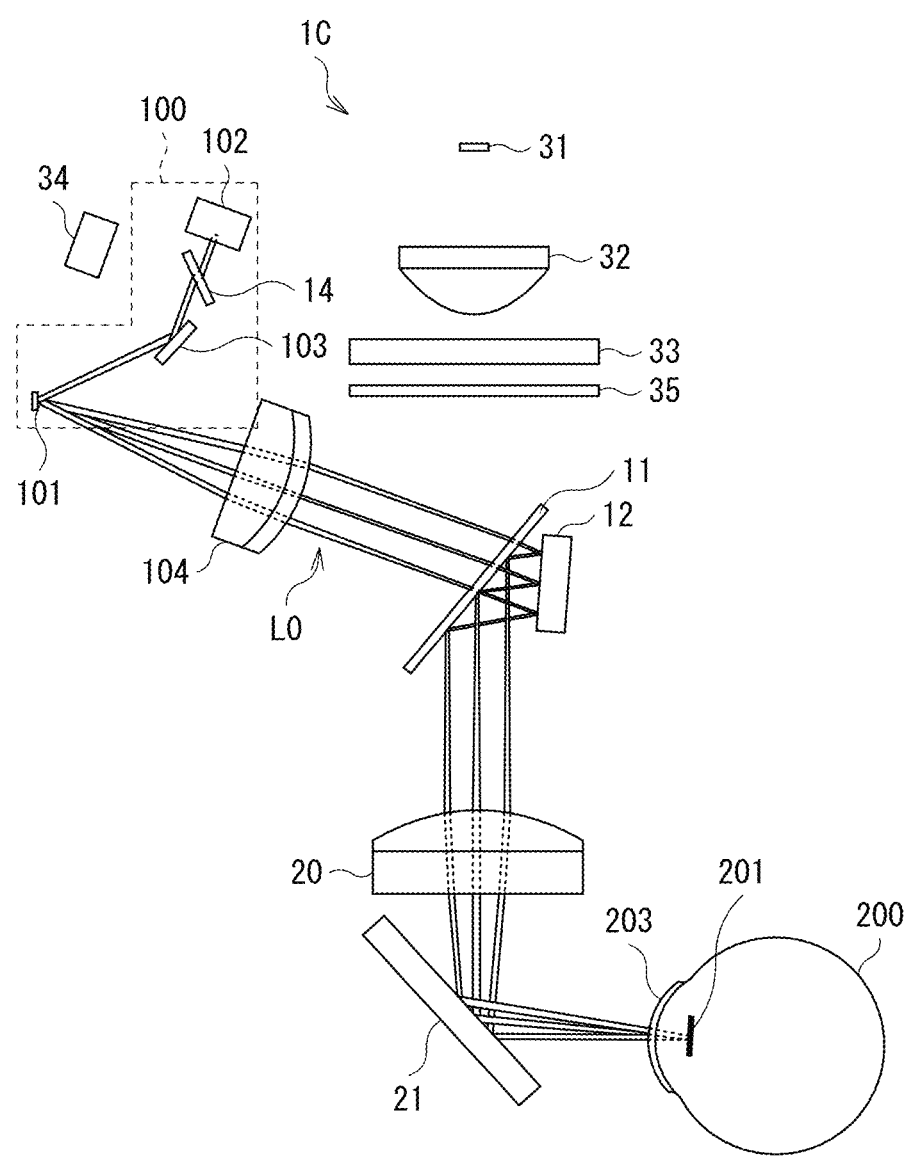

[FIG. 22]
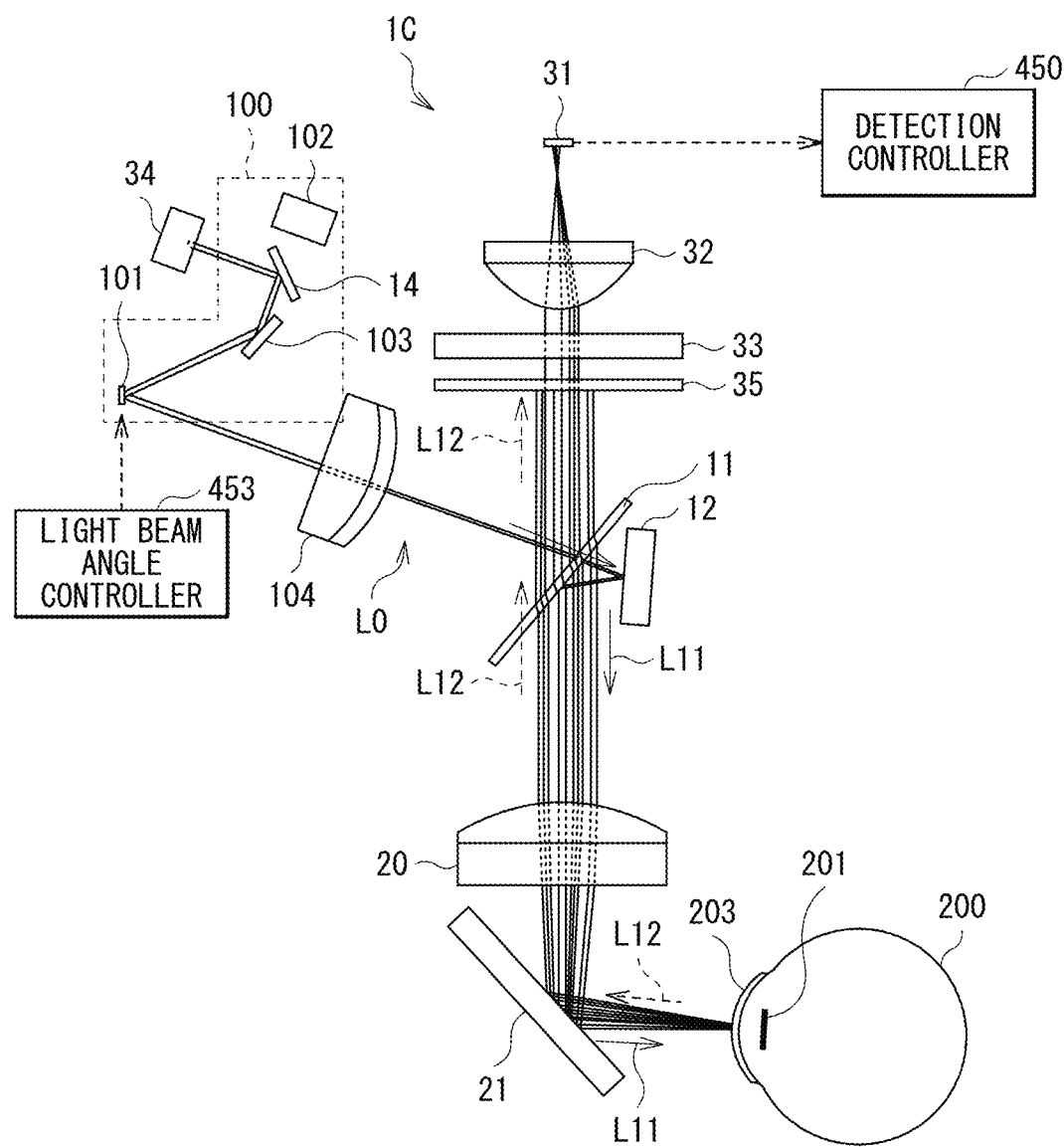

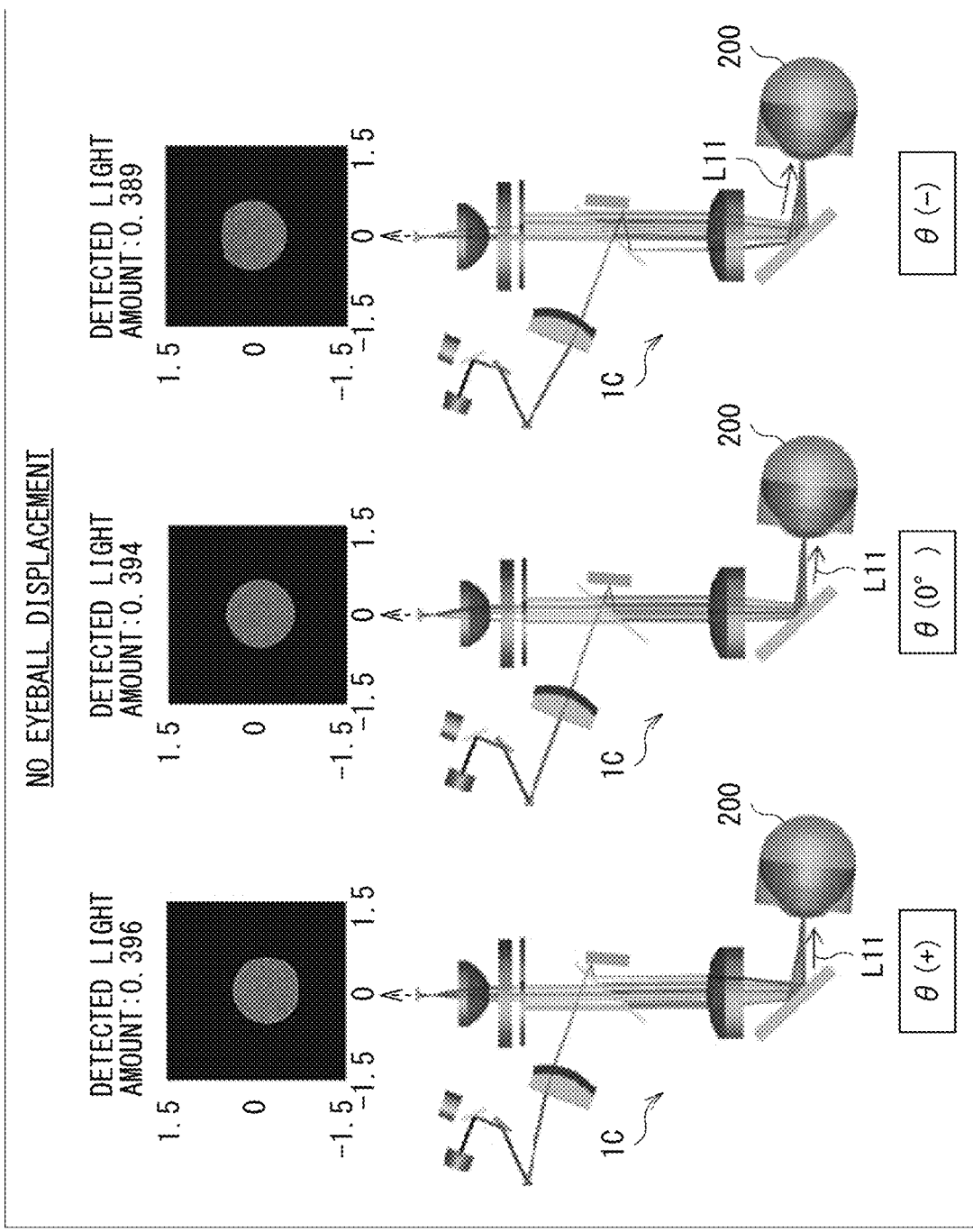
[FIG. 23]

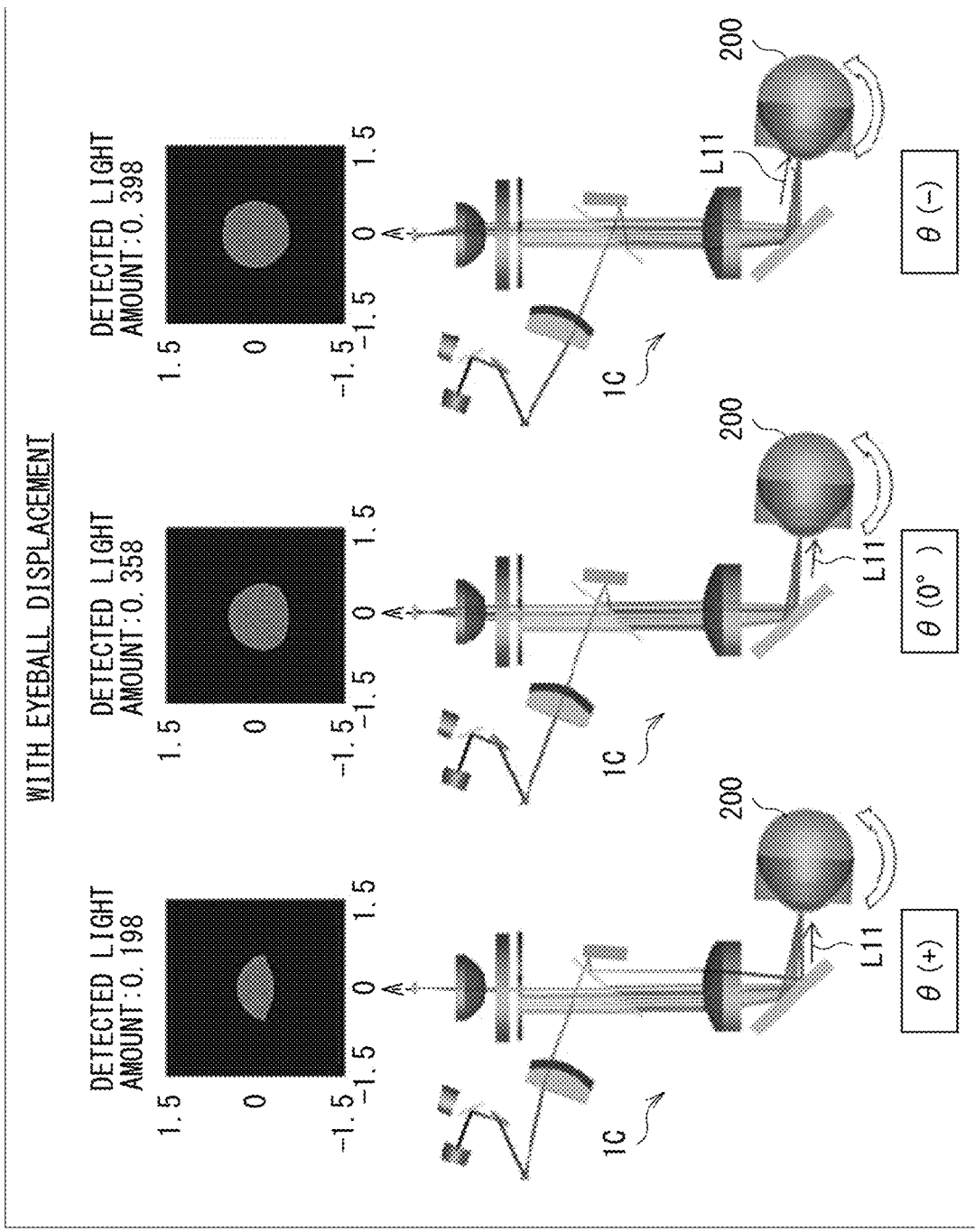
[FIG. 24]

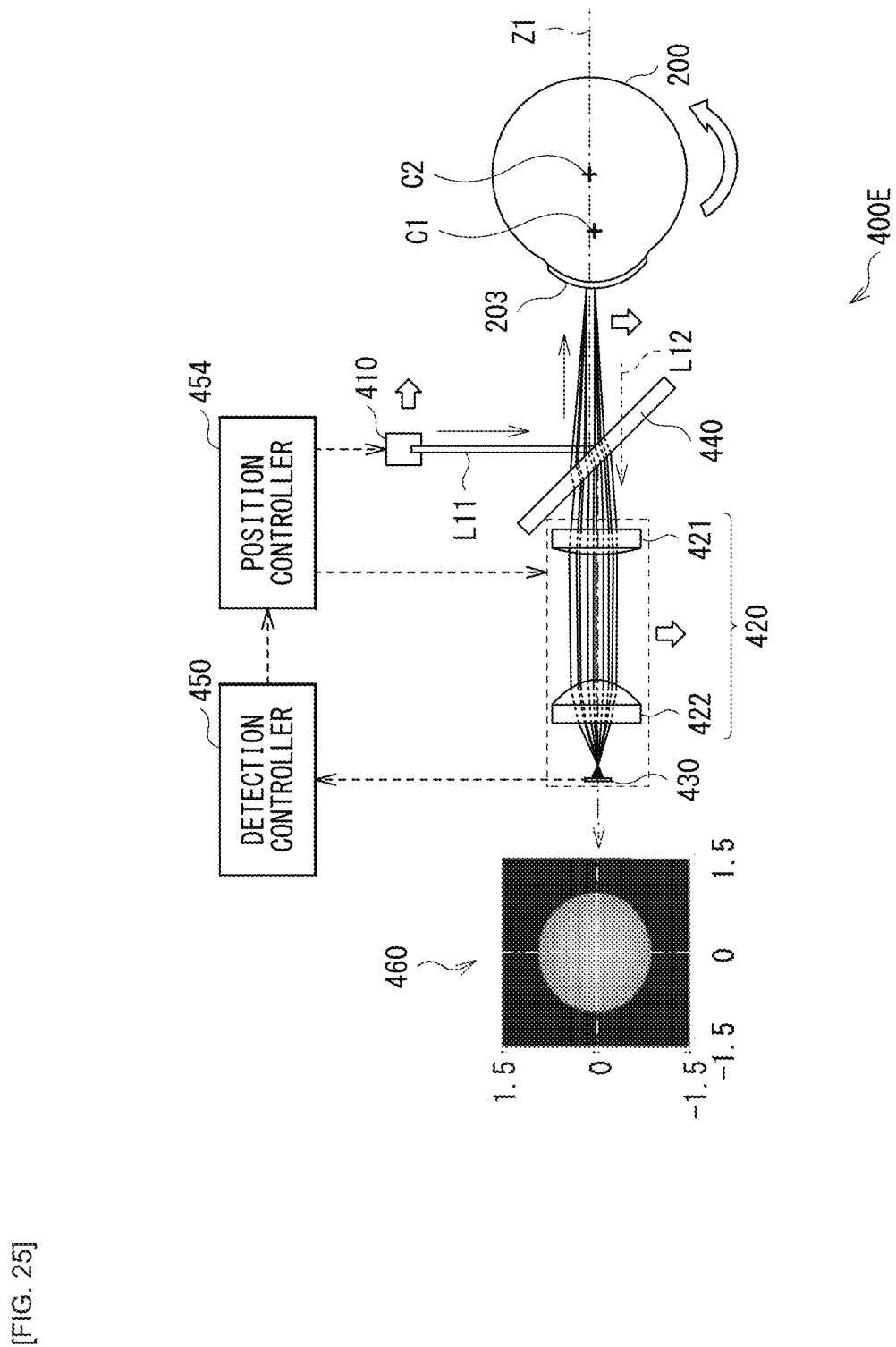
[FIG. 25]

[FIG. 26]
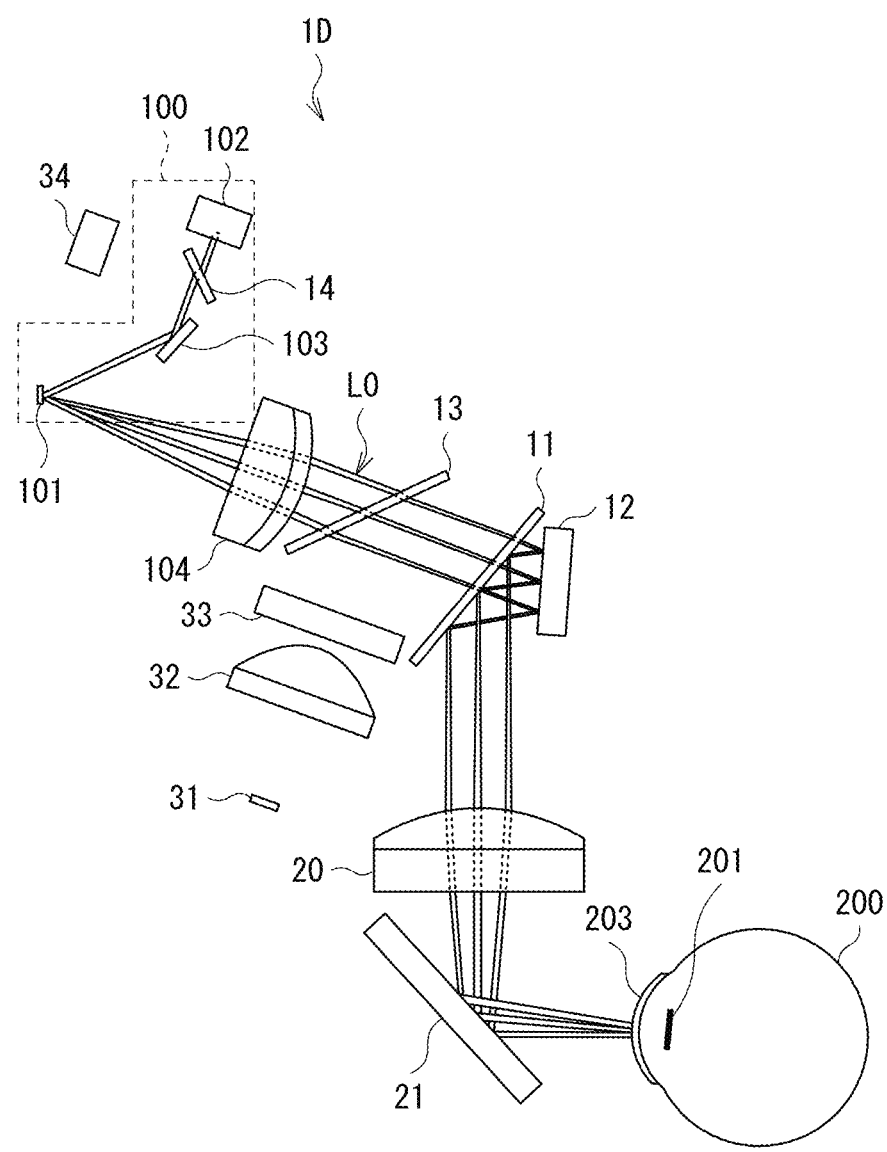

[FIG. 27]
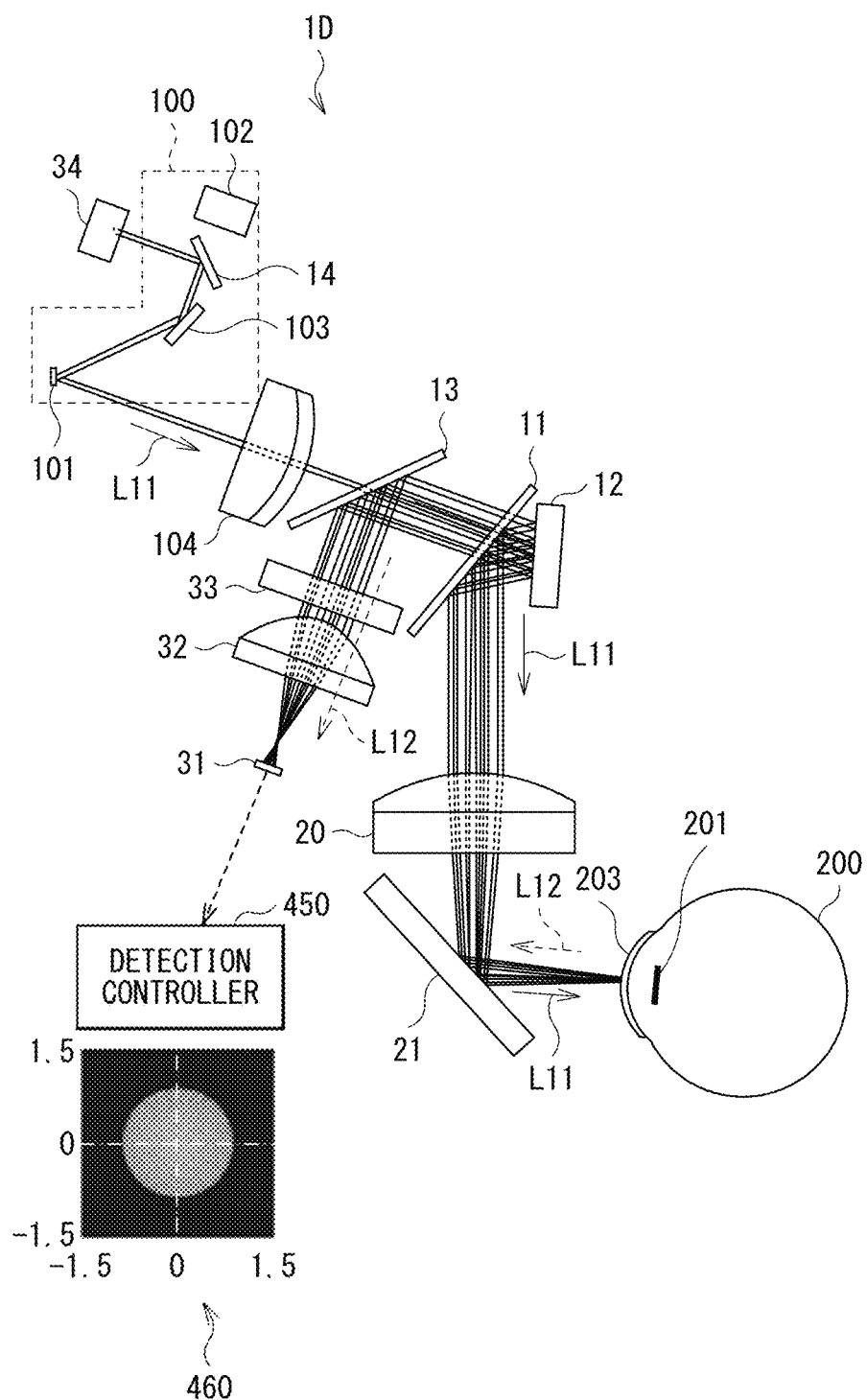

[FIG. 28]
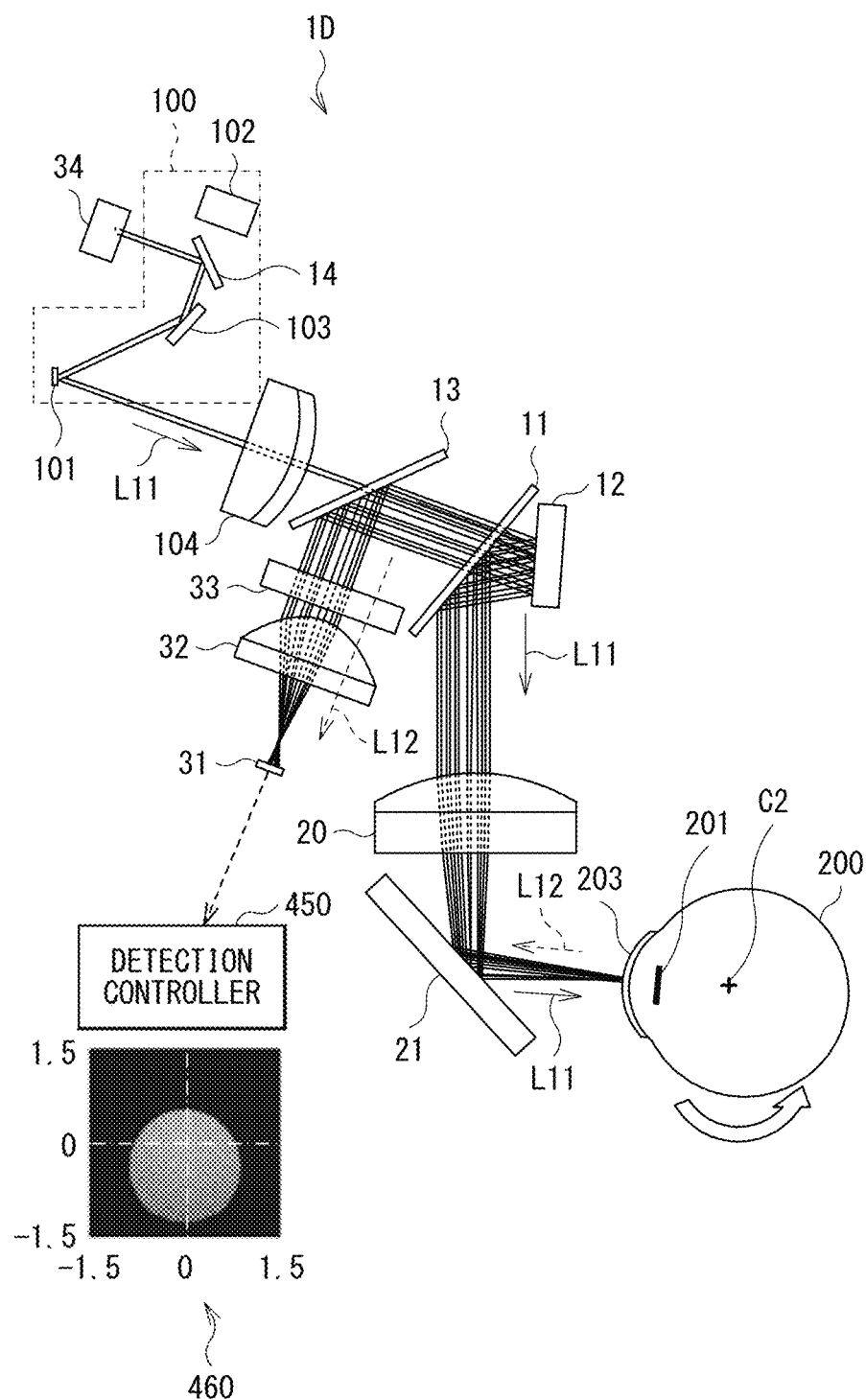

[FIG. 29]
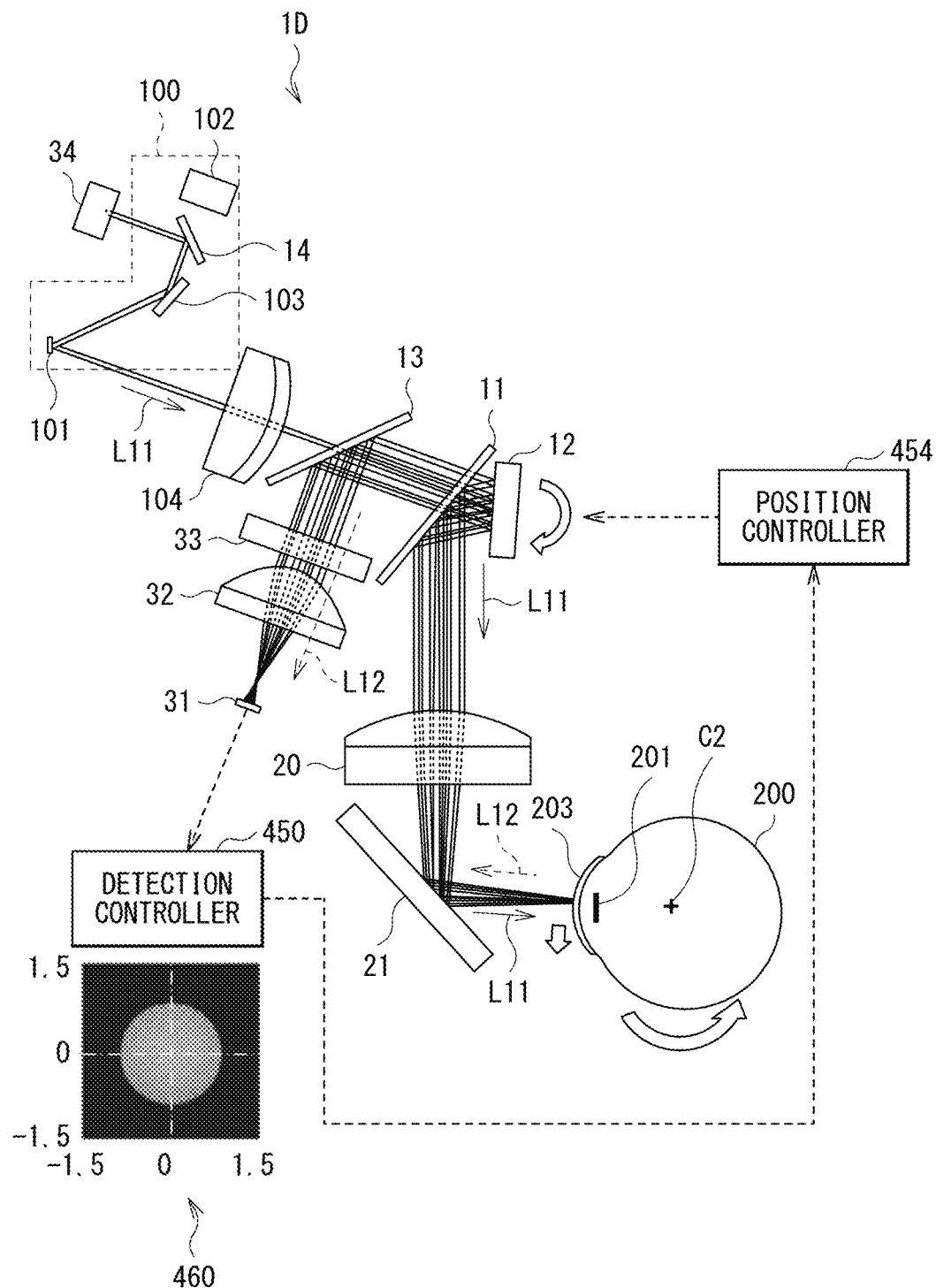

EYEBALL DETECTION UNIT AND IMAGE DISPLAY APPARATUS

CROSS REFERENCE TO RELATED APPLICATIONS

This application is a U.S. National Phase of International Patent Application No. PCT/JP2019/020646 filed on May 24, 2019, which claims priority benefit of Japanese Patent Application No. JP 2018-113779 filed in the Japan Patent Office on Jun. 14, 2018. Each of the above-referenced applications is hereby incorporated herein by reference in its entirety.

TECHNICAL FIELD

The present disclosure relates to an eyeball detection unit that detects a pupil position of a viewer, and an image display apparatus.

BACKGROUND ART

There has been an eyeball detection unit that detects a pupil position of a viewer by performing an image analysis (see PTLs 1 to 4). Meanwhile, an image display apparatus has been developed that generates image light by scanning light from a light source with a scan unit and guides the generated image light to a pupil of a viewer. Such an image display apparatus has been utilized as a head-mounted display, for example. In such an image display apparatus, an eyeball detection unit is used to appropriately guide the image light to the pupil position of the viewer.

CITATION LIST

Patent Literature

PTL 1: Japanese Unexamined Patent Application Publication No. 2014-188322
PTL 2: Japanese Unexamined Patent Application Publication No. 2006-58505
PTL 3: Japanese Unexamined Patent Application Publication No. H09-325260
PTL 4: Japanese Unexamined Patent Application Publication No. H06-54807

SUMMARY OF THE INVENTION

Pupil position detection through an image analysis involves an analysis of a large amount of pixel data, which leads to a large load in arithmetic processing, and is therefore disadvantageous in terms of processing speed, cost, and power consumption. Furthermore, using diffused illumination light as detection-purpose illumination light also leads to large power consumption.

It is desirable to provide an eyeball detection unit and an image display apparatus that make it possible to perform pupil position detection with less arithmetic load and power consumption.

An eyeball detection unit according to an embodiment of the present disclosure includes an irradiator that projects substantially parallel illumination light toward a cornea of an eyeball, a detector that detects light intensity of reflected light from the cornea, and a detection controller that identifies a centroid offset in an angular direction of the light intensity of the reflected light from the cornea with respect to a reference optical axis on the basis of a detected value by the detector, and thereafter calculates a positional offset of a cornea position with respect to the reference optical axis.

An image display apparatus according to an embodiment of the present disclosure includes an image light formation unit that outputs image light, a condensing optical system that causes the image light to converge toward a cornea of a viewer, and an eyeball detection unit, the eyeball detection unit including an irradiator that projects substantially parallel illumination light toward the cornea of the eyeball, with a projection position thereof lying at substantially the same position as a convergence position of the image light, a detector that detects light intensity of reflected light from the cornea, and a detection controller that identifies a centroid offset in an angular direction of the light intensity of the reflected light from the cornea with respect to a reference optical axis on the basis of a detected value by the detector, and thereafter calculates a positional offset of a cornea position with respect to the reference optical axis.

According to the eyeball detection unit or the image display apparatus of the respective embodiments of the present disclosure, the substantially parallel illumination light is projected toward the cornea of the eyeball, and the light intensity of the reflected light from the cornea is detected. After a centroid offset in the angular direction of the light intensity of the reflected light from the cornea with respect to the reference optical axis is identified on the basis of the detected value, a positional offset of the cornea position with respect to the reference optical axis is calculated.

BRIEF DESCRIPTION OF DRAWINGS

FIG. 1 is a configuration diagram of a configuration example of an eyeball detection unit according to a first embodiment of the present disclosure, illustrating an example case where an eyeball is in a forward looking state.

FIG. 2 is a configuration diagram of the configuration example of the eyeball detection unit according to the first embodiment, illustrating an example case where the state of the eyeball is changed from the forward looking state.

FIG. 3 is an explanatory diagram illustrating an example of a detected image and detected values by a detector in the eyeball detection unit according to the first embodiment in the case where the eyeball is in the forward looking state.

FIG. 4 is an explanatory diagram illustrating an example of a detected image and detected values by the detector in the eyeball detection unit according to the first embodiment in the case where the state of the eyeball is changed from the forward looking state.

FIG. 5 is a configuration diagram illustrating a preferable example of a detection position of the detector in the eyeball detection unit according to the first embodiment.

FIG. 6 is a configuration diagram illustrating a comparative example relative to the eyeball detection unit illustrated in FIG. 5.

FIG. 7 is a configuration diagram illustrating a configuration example of an image display apparatus according to the first embodiment together with an optical path of image light.

FIG. 8 is a configuration diagram illustrating a configuration example of the image display apparatus according to the first embodiment together with an optical path at the time of pupil position detection in the case where the eyeball is in the forward looking state.

FIG. 9 is a configuration diagram illustrating a configuration example of the image display apparatus according to the first embodiment together with an optical path at the time of pupil position detection in the case where the state of the eyeball is changed from the forward looking state.

FIG. 10 is a configuration diagram of a configuration example of an eyeball detection unit according to a second embodiment, illustrating an example case where the state of the eyeball is changed from the forward looking state.

FIG. 11 is a configuration diagram illustrating a configuration example of an image display apparatus according to the second embodiment together with an optical path at the time of pupil position detection in the case where the state of the eyeball is changed from the forward looking state.

FIG. 12 is a configuration diagram of a configuration example of an eyeball detection unit according to a third embodiment, illustrating an example case where the state of the eyeball is changed from the forward looking state.

FIG. 13 is a configuration diagram illustrating a configuration example of an image display apparatus according to the third embodiment together with an optical path at the time of pupil position detection in the case where the state of the eyeball is changed from the forward looking state.

FIG. 14 is a configuration diagram illustrating a configuration example of the image display apparatus according to the third embodiment together with an optical path at the time of pupil position detection in a case where the state of the eyeball is changed from the forward looking state and also a projection position of illumination light and a detection position are caused to move.

FIG. 15 is an explanatory diagram illustrating an example of a relationship table used in an eyeball detection unit according to a fourth embodiment.

FIG. 16 is a flowchart illustrating an example of an operation of pupil position detection in the eyeball detection unit according to the fourth embodiment.

FIG. 17 is an explanatory diagram illustrating, with use of the relationship table, an example of the operation of pupil position detection in the eyeball detection unit according to the fourth embodiment.

FIG. 18 is a configuration diagram of a configuration example of an eyeball detection unit according to a fifth embodiment, illustrating an example case where a projection angle of the illumination light is set to 0° in the case where the state of the eyeball is changed from the forward looking state.

FIG. 19 is a configuration diagram of a configuration example of the eyeball detection unit according to the fifth embodiment, illustrating an example case where the projection angle of the illumination light is moved in a + direction in the case where the state of the eyeball is changed from the forward looking state.

FIG. 20 is a configuration diagram of a configuration example of the eyeball detection unit according to the fifth embodiment, illustrating an example case where the projection angle of the illumination light is moved in a − direction in the case where the state of the eyeball is changed from the forward looking state.

FIG. 21 is a configuration diagram illustrating a configuration example of an image display apparatus according to the fifth embodiment together with an optical path of the image light.

FIG. 22 is a configuration diagram illustrating a configuration example of the image display apparatus according to the fifth embodiment together with an optical path at the time of pupil position detection in the case where the eyeball is in the forward looking state.

FIG. 23 is an explanatory diagram illustrating an example of detected images and detected light amounts in a case where the projection angle of the illumination light is changed in the image display apparatus according to the fifth embodiment while the eyeball is in the forward looking state.

FIG. 24 is an explanatory diagram illustrating an example of detected images and detected light amounts in the case where the projection angle of the illumination light is changed in the image display apparatus according to the fifth embodiment, with the state of the eyeball being changed from the forward looking state.

FIG. 25 is a configuration diagram of a configuration example of an eyeball detection unit according to a sixth embodiment, illustrating an example case where the state of the eyeball is changed from the forward looking state.

FIG. 26 is a configuration diagram illustrating a configuration example of an image display apparatus according to the sixth embodiment together with an optical path of the image light.

FIG. 27 is a configuration diagram illustrating a configuration example of the image display apparatus according to the sixth embodiment together with an optical path at the time of pupil position detection in the case where the eyeball is in the forward looking state.

FIG. 28 is a configuration diagram illustrating a configuration example of the image display apparatus according to the sixth embodiment together with an optical path at the time of pupil position detection in the case where the state of the eyeball is changed from the forward looking state.

FIG. 29 is a configuration diagram illustrating a configuration example of the image display apparatus according to the sixth embodiment together with an optical path at the time of pupil position detection in the case where the state of the eyeball is changed from the forward looking state and also the projection position of the illumination light and the detection position are caused to move.

MODES FOR CARRYING OUT THE INVENTION

Some embodiments of the present disclosure are described in detail below with reference to the drawings. It is to be noted that descriptions are given in the following order.

1. First Embodiment
 1.1. Configuration and Operation of Eyeball Detection Unit According to First Embodiment (FIGS. 1 to 6)
 1.2. Configuration and Operation of Image Display Apparatus According to First Embodiment (FIGS. 7 to 9)
 1.3. Effects
2. Second Embodiment (FIGS. 10 to 11)
3. Third Embodiment (FIGS. 12 to 14)
4. Fourth Embodiment (FIGS. 15 to 17)
5. Fifth Embodiment (FIGS. 18 to 24)
6. Sixth Embodiment (FIGS. 25 to 29)
7. Other Embodiments 1. First Embodiment

[1.1. Configuration and Operation of Eyeball Detection Unit According to First Embodiment]
(Outline of Eyeball Detection Unit)

FIGS. 1 and 2 each illustrate a configuration example of an eyeball detection unit 400 according to a first embodiment of the present disclosure. FIG. 1 illustrates the configuration example of the eyeball detection unit 400 in an example case where an eyeball 200 is in a forward looking state. FIG. 2 illustrates the configuration example of the eyeball detection unit 400 in an example case where the state of the eyeball 200 is changed from the forward looking state.

The eyeball detection unit 400 includes an irradiator 410, a detection optical system 420, a detector 430, a half mirror 440, and a detection controller 450.

The irradiator 410 projects substantially parallel illumination light L11 toward a cornea 203 of the eyeball 200 of a viewer. The illumination light L11 is infrared light, for example. The irradiator 410 includes an illumination light source such as an IR (infrared) laser diode that emits infrared light, for example.

The detector 430 detects light intensity of reflected light L12 from the cornea 203. The detector 430 includes a detection device such as a photodiode or an image sensor, for example.

The half mirror 440 is disposed to reflect the illumination light L11 from the irradiator 410 toward the cornea 203 of the eyeball 200. The half mirror 440 is disposed to allow the reflected light L12 from the cornea 203 to pass through toward the detection optical system 420.

The detection optical system 420 is disposed on an optical path between the half mirror 440 and the detector 430. The detection optical system 420 includes a condenser lens 421 and a condensing and detection optical system 422. The condensing and detection optical system 422 condenses the reflected light L12 from the cornea 203 toward the detector 430.

The detection controller 450 identifies a centroid offset in an angular direction of the light intensity of the reflected light L12 from the cornea 203 with respect to a reference optical axis Z1 on the basis of a detected value (a detected image 460) by the detector 430, and thereafter calculates a positional offset of a cornea position with respect to the reference optical axis Z1.

Here, the reference optical axis Z1 is a straight line including a center of curvature of the cornea 203 (a cornea curvature center C1) when the eyeball 200 is in the forward looking state and a center of rotation of the eyeball 200 (an eyeball rotation center C2). The detection controller 450 detects, as the positional offset of the cornea position, a positional offset of the center of curvature of the cornea 203 (the cornea curvature center C1) with respect to the reference optical axis Z1.

(Example of Detected Value)

FIGS. 3 and 4 each illustrate an example of the detected image 460 and detected values by the detector 430. FIG. 3 illustrates an example of the detected image 460 and the detected values in the eyeball detection unit 400 in a case where the eyeball 200 is in the forward looking state (see FIG. 1). FIG. 4 illustrates an example of the detected image 460 and the detected values in the eyeball detection unit 400 in a case where the state of the eyeball 200 is changed from the forward looking state (see FIG. 2).

The detector 430 includes a plurality of divided detection regions. FIGS. 3 and 4 each illustrate an example where four divided detection regions are provided; however, the number of the divided detection regions may be three or less, or five or more.

On the basis of a detected value of an intensity of received light in each of the plurality of divided detection regions, the detection controller 450 identifies a centroid offset in the angular direction of the light intensity of the reflected light L12 from the cornea 203 with respect to the reference optical axis Z1.

As illustrated in FIGS. 3 and 4, the centroid offset in the angular direction with respect to the reference optical axis Z1 changes with a change in the eyeball 200 (a change in a pupil position). It is thus possible for the detection controller 450 to calculate the positional offset of the cornea position on the basis of the centroid offset.

As described above, in the eyeball detection unit 400, a positional offset of the cornea position is calculated by detecting a rough distribution of the light intensity (a centroid offset in the angular direction) of the reflected light L12, not by performing a detailed image analysis of the detected image 460.

(Example of Detection Position)

FIG. 5 illustrates a preferable example of a detection position of the detector 430 in the eyeball detection unit 400. FIG. 6 illustrates an eyeball detection unit 400A according to a comparative example relative to the eyeball detection unit 400 illustrated in FIG. 5.

In the eyeball detection unit 400A according to the comparative example illustrated in FIG. 6, the detector 430 is disposed at substantially the same position as a focal position Pf on the detector-430 side of the condensing and detection optical system 422. In a case where the detector 430 is disposed at substantially the same position as the focal position Pf as with the eyeball detection unit 400A according to the comparative example illustrated in FIG. 6, it becomes difficult for the detection controller 450 to identify a change in the centroid offset of the reflected light L12 on the basis of a result of detection by the detector 430.

Therefore, instead of the arrangement illustrated in FIG. 6, it is desirable that the detector 430 be disposed at a position off the focal position Pf on the detector-430 side of the condensing and detection optical system 422, as illustrated in FIG. 5. It is to be noted that FIG. 5 illustrates an example where the detector 430 is disposed at a position that is off the focal position Pf in a direction away from the condensing and detection optical system 422; however, the detector 430 may be disposed at a position that is off the focal position Pf in a direction approaching the condensing and detection optical system 422. This makes it easy for the detection controller 450 to identify a change in the centroid offset of the reflected light L12 on the basis of the result of detection by the detector 430.

[1.2 Configuration and Operation of Image Display Apparatus According to First Embodiment]

FIGS. 7 to 9 each illustrate a configuration example of an image display apparatus 1 according to the first embodiment. FIG. 7 illustrates the configuration example of the image display apparatus 1 together with an optical path of image light L0. FIG. 8 illustrates the configuration example of the image display apparatus 1 together with an optical path at the time of pupil position detection in a case where the eyeball 200 is in the forward looking state. FIG. 9 illustrates the configuration example of the image display apparatus 1 together with an optical path at the time of pupil position detection in a case where the state of the eyeball 200 is changed from the forward looking state.

(Outline of Image Display Apparatus)

The image display apparatus 1 according to the first embodiment includes an image light formation unit 100 that generates the image light L0, and a condensing optical system 20 that causes the image light L0 to converge toward the cornea 203 of the viewer. The image display apparatus 1 is an apparatus that guides the image light L0 generated by the image light formation unit 100 to the pupil position of the viewer, and is usable as, for example, a head-mounted display.

The image display apparatus 1 includes an image display system including the image light formation unit 100 (see FIG. 7), and a detection system that detects the pupil position of the viewer (see FIGS. 8 and 9). The detection system has a configuration corresponding to the eyeball detection unit 400 described above. In the detection system, the substantially parallel illumination light L11 is projected toward the cornea 203 of the eyeball 200, with the projection position thereof lying at substantially the same position as a convergence position of the image light L0, and the reflected light L12 from the cornea 203 is detected. The image display apparatus 1 causes the projection position of the illumination light L11 and the convergence position of the image light L0 to lie at substantially the same position, thereby enabling the image light L0 to converge accurately at a specific pupil position.

(Outline of Image Display System)

The image display apparatus 1 includes, as components of the image display system, the image light formation unit 100, a first reflective device 11, a second reflective device 12, the condensing optical system 20, a half mirror 21, a collimator lens 104, and a light beam position controller 451.

The image light formation unit 100 generates the image light L0, and outputs the generated image light L0. The image light formation unit 100 includes a scanning mirror 101, a drawing light source 102, and a total reflective mirror 103.

The drawing light source 102 is a laser light source including a laser diode, for example. The drawing light source 102 may include a plurality of laser diodes that emits red (R), green (G), and blue (B) light. The drawing light source 102 outputs laser light having undergone intensity modulation based on image data toward the scanning mirror 101. An optical system that guides laser light from the drawing light source 102 to the scanning mirror 101 may be disposed between the drawing light source 102 and the scanning mirror 101.

The scanning mirror 101 includes, for example, a MEMS (Micro Electro Mechanical Systems) mirror. The scanning mirror 101 generates two-dimensional image light L0 by two-dimensionally scanning the laser light from the drawing light source 102 on the basis of the image data. A scanning direction and a scanning timing of the scanning mirror 101 are controlled on the basis of the image data.

The image light formation unit 100 is not limited to such a laser-scanning unit that uses the drawing light source 102 and the scanning mirror 101 but may be a unit that uses a display panel and a pinhole. For example, a unit that condenses image light from a display panel such as a liquid crystal display (LCD: Liquid Crystal Display) or an organic electro-luminescence display (OELD: Organic Electro-Luminescence Display) to a pinhole using a condenser lens and outputs the condensed image light toward the collimator lens 104 may be used.

The collimator lens 104 causes the traveling directions of beams from respective pixels in the image light formation unit 100 to be in parallel to each other, and causes the beams to enter the first reflective device 11 as the image light L0.

The first reflective device 11 is a half mirror having a transmitting function and a reflecting function on the image light L0. The image light L0 from the image light formation unit 100 enters the second reflective device 12 via the first reflective device 11.

The second reflective device 12 is a total reflective mirror having a reflective function on the image light L0. The second reflective device 12 reflects the image light L0 that has entered via the first reflective device 11 toward the first reflective device 11, and causes the image light L0 to enter the first reflective device 11 again.

The second reflective device 12 is disposed on a first transmission optical path of the image light L0 from the image light formation unit 100 after passing through the first reflective device 11. The first reflective device 11 is disposed to reflect the image light L0 that has been reflected by the second reflective device 12 and has entered again the first reflective device 11 toward the condensing optical system 20.

The condensing optical system 20 is an optical system that causes the image light L0 that has entered again the first reflective device 11 to converge toward the pupil position of the viewer via the half mirror 21. The condensing optical system 20 includes at least one condensing device such as a condenser lens.

The half mirror 21 is disposed on an optical path between the condensing optical system 20 and the pupil position of the viewer. The half mirror 21 is disposed to face the eyeball 200 of the viewer. The viewer views the image light L0 via the half mirror 21. Therefore, in a case where the image display apparatus 1 is configured as a head-mounted display, for example, it is possible to view the image light L0 formed by the image light formation unit 100 and also view an external scene in a see-through manner.

The detection system includes a detection device 31 and the detection controller 450, as will be described later. The detection controller 450 detects a positional offset of the cornea position of the viewer on the basis of the result of detection by the detection device 31.

The light beam position controller 451 causes the convergence position of the image light L0 to move to an appropriate position on the basis of the positional offset of the cornea position detected by the detection controller 450 of the detection system. As a result, it is possible to cause also the projection position of the illumination light L11 to move to an appropriate position. The light beam position controller 451 controls a disposition angle of the second reflective device 12 on the basis of the detected positional offset of the cornea position, for example. This makes it possible to guide the image light L0 to a pupil 201 of the viewer regardless of a movement of the pupil position of the viewer.

(Outline of Detection System)

The image display apparatus 1 includes, as components of the detection system, a third reflective device 13, the detection device 31, an imaging lens 32, a wavelength cut filter 33, an illumination light source 34, and the detection controller 450.

In the image display apparatus 1, at least the illumination light source 34 and the third reflective device 13 correspond to the irradiator 410 in the eyeball detection unit 400 described above. In the image display apparatus 1, at least the detection device 31 corresponds to the detector 430 in the eyeball detection unit 400 described above.

The illumination light source 34 emits the illumination light L11 for detection of the pupil position of the viewer. The illumination light L11 is infrared light, for example. The illumination light source 34 is an IR (infrared) laser diode that emits infrared light, for example.

The third reflective device 13 is a half mirror, and reflects the illumination light L11 emitted from the illumination light source 34 to cause the reflected light to enter the first reflective device 11. Further, the third reflective device 13 allows the image light L0 to pass through. The illumination light L11 that has entered the first reflective device 11 travels on an optical path that is substantially the same as that of the image light L0, and irradiates the pupil position (the eyeball 200) of the viewer. As with the convergence position of the image light L0, the projection position of the illumination light L11 is adjusted in accordance with a change in the pupil position of the viewer by, for example, controlling the disposition angle of the second reflective device 12.

The illumination light L11 is reflected at the cornea 203 of the eyeball 200. The reflected light L12 from the cornea 203 is thereby generated.

The detection device 31 is disposed on a second transmission optical path of the reflected light L12 that has been reflected by the eyeball 200 of the viewer, has traveled backward in the condensing optical system 20 and has passed through the first reflective device 11, to detect the reflected light L12. The wavelength cut filter 33 and the imaging lens 32 are disposed on the second transmission optical path between the first reflective device 11 and the detection device 31.

The wavelength cut filter 33 is a filter that cuts light in wavelength bands other than a wavelength band of the illumination light L11, and is a visible-light cut filter, for example.

In the detection system, the detection controller 450 calculates the positional offset of the cornea position on a principle similar to that of the eyeball detection unit 400 described above.

[1.3. Effects]

As described above, according to the eyeball detection unit and the image display apparatus of the first embodiment, a centroid offset in the angular direction of the light intensity of the reflected light L12 from the cornea 203 with respect to the reference optical axis Z1 is identified on the basis of the detected value of the light intensity of the reflected light L12 from the cornea 203, and thereafter a positional offset of the cornea position with respect to the reference optical axis Z1 is calculated. This makes it possible to perform pupil position detection with less arithmetic load and power consumption.

According to the eyeball detection unit and the image display apparatus of the first embodiment, the divided detection regions of the detector 430 are small in number and therefore it is possible to detect the pupil position with simple arithmetic processing without having to perform image analysis. This improves latency and power consumption associated with image analysis. Furthermore, the employment of the method of detecting the reflected light L12 having a higher directional characteristic results in smaller loss of the detected light amount with respect to the irradiation light amount, thus making power consumption of the illumination light source smaller, compared with the method of detecting diffused reflected light, for example. With the eyeball detection unit and the image display apparatus according to the first embodiment, it is possible to illuminate the cornea 203 with a minimum light amount (small-diameter beams) and to detect the pupil position with only a minimum number of detected values.

It is to be noted that the effects described herein are mere examples and non-limiting, and other effects may also be provided. This also holds true for effects of other subsequent embodiments.

2. Second Embodiment

Next, an eyeball detection unit and an image display apparatus according to a second embodiment of the present disclosure will be described. It is to be noted that, in the following, components substantially the same as those of the eyeball detection unit and the image display apparatus according to the foregoing first embodiment are denoted with the same reference numerals, and the description thereof is omitted where appropriate.

(Configuration and Operation of Eyeball Detection Unit)

FIG. 10 illustrates a configuration example of an eyeball detection unit 400B according to the second embodiment. FIG. 10 illustrates the configuration example of the eyeball detection unit 400B in an example case where the state of the eyeball 200 is changed from the forward looking state.

Relative to the configuration of the eyeball detection unit 400 according to the first embodiment described above, the eyeball detection unit 400B further includes the light beam position controller 451. The light beam position controller 451 causes, on the basis of an instruction from the detection controller 450, the projection position of the illumination light L11 to the cornea 203 to move with respect to the reference optical axis Z1.

In the eyeball detection unit 400B, on the basis of the detected value by the detector 430, the detection controller 450 instructs the light beam position controller 451 to cause the projection position of the illumination light L11 to move to reduce the centroid offset in the angular direction of the light intensity of the reflected light L12 from the cornea 203 with respect to the reference optical axis Z1. Further, the detection controller 450 calculates the positional offset of the cornea position on the basis of the amount of movement of the projection position of the illumination light L11.

(Configuration and Operation of Image Display Apparatus)

FIG. 11 illustrates a configuration example of an image display apparatus 1A according to the second embodiment. FIG. 11 illustrates the configuration example of the image display apparatus 1A together with an optical path at the time of pupil position detection in the case where the state of the eyeball 200 is changed from the forward looking state.

The image display apparatus 1A includes an image display system including the image light formation unit 100, and a detection system that detects the pupil position of the viewer (see FIG. 11), substantially similarly to the configuration of the image display apparatus 1 according to the foregoing first embodiment. The detection system has a configuration corresponding to the eyeball detection unit 400B described above.

In the image display apparatus 1A, as an operation of the detection system, the detection controller 450 instructs, on the basis of the detected value by the detection device 31, the light beam position controller 451 to cause the projection position of the illumination light L11 to move to reduce the centroid offset in the angular direction of the light intensity of the reflected light L12 from the cornea 203 with respect to the reference optical axis Z1. On the basis of the instruction from the detection controller 450, the light beam position controller 451 causes the projection position of the illumination light L11 to the cornea 203 to move with respect to the reference optical axis Z1 by controlling, for example, the disposition angle of the second reflective device 12. As a result, it is possible to cause the projection position of the illumination light L11 and the convergence position of the image light L0 to move to appropriate positions.

The remainder of the configuration, operations, and effects may be substantially similar to those of the eyeball detection unit and the image display apparatus according to the foregoing first embodiment.

3. Third Embodiment

Next, an eyeball detection unit and an image display apparatus according to a third embodiment of the present disclosure will be described. It is to be noted that, in the following, components substantially the same as those of the eyeball detection unit and the image display apparatus according to the foregoing first or second embodiment are denoted with the same reference numerals, and the description thereof is omitted where appropriate.

(Configuration and Operation of Eyeball Detection Unit)

FIG. 12 illustrates a configuration example of an eyeball detection unit 400C according to the third embodiment. FIG. 12 illustrates the configuration example of the eyeball detection unit 400C in an example case where the state of the eyeball 200 is changed from the forward looking state.

Relative to the configuration of the eyeball detection unit 400 according to the foregoing first embodiment, the eyeball detection unit 400C further includes the light beam position controller 451 and a detection position controller 452.

The light beam position controller 451 causes, on the basis of an instruction from the detection controller 450, the projection position of the illumination light L11 to the cornea 203 to move with respect to the reference optical axis Z1.

The detection position controller 452 causes, on the basis of an instruction from the detection controller 450, the detection position of the light intensity by the detector 430 to move.

In the eyeball detection unit 400C, on the basis of the detected value by the detector 430, the detection controller 450 instructs the light beam position controller 451 to cause the projection position of the illumination light L11 to move to reduce the centroid offset in the angular direction of the light intensity of the reflected light L12 from the cornea 203 with respect to the reference optical axis Z1.

On the basis of the amount of movement of the projection position of the illumination light L11, the detection controller 450 instructs the detection position controller 452 to cause the detection position to move. Further, the detection controller 450 calculates the positional offset of the cornea position on the basis of the amount of movement of the projection position of the illumination light L11 and the amount of movement of the detection position.

In the eyeball detection unit 400C, the projection position of the illumination light L11 is caused to move in accordance with a change in the pupil position to thereby bring the reflected light L12 back onto the reference optical axis Z1. Furthermore, in the eyeball detection unit 400C, the detection position is corrected to make it possible to detect the reflected light L12 at a substantially central position in the detector 430 in response to a change in the pupil position. This makes it possible to detect more accurately the light intensity of the reflected light L12 from the cornea 203.

(Configuration and Operation of Image Display Apparatus)

FIGS. 13 and 14 each illustrate a configuration example of an image display apparatus 1B according to the third embodiment. FIG. 13 illustrates the configuration example of the image display apparatus 1B together with an optical path at the time of pupil position detection in the case where the state of the eyeball 200 is changed from the forward looking state. FIG. 14 illustrates the configuration example of the image display apparatus 1B together with an optical path at the time of pupil position detection in a case where the state of the eyeball 200 is changed from the forward looking state and also the projection position of the illumination light L12 and the detection position are caused to move.

The image display apparatus 1B includes an image display system including the image light formation unit 100, and a detection system that detects the pupil position of the viewer (see FIGS. 13 and 14), substantially similarly to the configuration of the image display apparatus 1 according to the foregoing first embodiment. The detection system has a configuration corresponding to the eyeball detection unit 400C described above.

In the image display apparatus 1B, as an operation of the detection system, the detection controller 450 instructs, on the basis of the detected value by the detection device 31, the light beam position controller 451 to cause the projection position of the illumination light L11 to move to reduce the centroid offset in the angular direction of the light intensity of the reflected light L12 from the cornea 203 with respect to the reference optical axis Z1. On the basis of the instruction from the detection controller 450, the light beam position controller 451 causes the projection position of the illumination light L11 to the cornea 203 to move with respect to the reference optical axis Z1 by controlling, for example, the disposition angle of the second reflective device 12. As a result, it is possible to cause the projection position of the illumination light L11 and the convergence position of the image light L0 to move to appropriate positions.

Further, in the image display apparatus 1B, as an operation of the detection system, the detection controller 450 instructs, on the basis of the amount of movement of the projection position of the illumination light L11, the detection position controller 452 to cause the detection position to move. On the basis of the instruction from the detection controller 450, the detection position controller 452 controls, for example, the arrangement positions of the detection device 31 and the imaging lens 32 to thereby cause the detection position of the light intensity by the detection device 31 to move. As a result, the detection position is corrected to make it possible to detect the reflected light L12 at a substantially central position in the detection device 31 in response to a change in the pupil position.

The remainder of the configuration, operations, and effects may be substantially similar to those of the eyeball detection unit and the image display apparatus according to the foregoing first embodiment.

4. Fourth Embodiment

Next, an eyeball detection unit and an image display apparatus according to a fourth embodiment of the present disclosure will be described. It is to be noted that, in the following, components substantially the same as those of the eyeball detection unit and the image display apparatus according to any one of the foregoing first to third embodiments are denoted with the same reference numerals, and the description thereof is omitted where appropriate.

The eyeball detection unit according to the fourth embodiment further includes the light beam position controller 451, as with the eyeball detection unit 400B according to the foregoing second embodiment. On the basis of an instruction from the detection controller 450, the light beam position controller 451 causes the projection position of the illumination light L11 to the cornea 203 to move with respect to the reference optical axis Z1.

Relative to the configuration of the eyeball detection unit 400B according to the foregoing second embodiment, the eyeball detection unit according to the fourth embodiment uses a different method of calculation of a positional offset of the cornea position by the detection controller 450.

In the eyeball detection unit according to the fourth embodiment, the detection controller 450 stores a relationship table of reference values of centroid offsets associated with amounts of movement of the projection position of the illumination light L11 and positional offsets of the cornea position and, by referencing the relationship table, calculates a positional offset of the cornea position on the basis of an amount of movement of the projection position of the illumination light L11 and a centroid offset identified on the basis of the detected value by the detector 430.

FIG. 15 illustrates an example of the relationship table used in the eyeball detection unit according to the fourth embodiment. FIG. 16 illustrates an example of operation of pupil position detection in the eyeball detection unit according to the fourth embodiment. FIG. 17 illustrates, with reference to the relationship table, an example of the operation of pupil position detection in the eyeball detection unit according to the fourth embodiment.

The operation of the eyeball detection unit according to the fourth embodiment at the time of pupil position detection will now be described in line with the operation flows illustrated in FIGS. 16 and 17.

The detection controller 450 first identifies the current projection position of the illumination light L11 to the cornea 203 on the basis of the amount of movement of the projection position of the illumination light L11 by the light beam position controller 451 (step S1). In the example in FIG. 17, the projection position identified at step S1 is 0 (mm) with respect to the reference optical axis Z1.

Next, the detection controller 450 identifies a centroid offset on the basis of the detected value by the detector 430 (step S2). Next, the detection controller 450 references the relationship table and calculates a positional offset of the cornea position (step S3). In the example in FIG. 17, the detected value by the detector 430 is identified as corresponding to, for example, a reference value of a centroid offset located at the second position from the left in the topmost row of the relationship table, and the presence of a centroid offset corresponding to a positional offset of the cornea position of 0.8 (mm) (an angle of rotation of the eyeball is 5°) is thus identified.

Next, by referencing the relationship table, the detection controller 450 calculates an optimum projection position for the calculated positional offset of the cornea position, and instructs the light beam position controller 451 to cause the projection position of the illumination light L11 to move to approach the calculated optimum projection position (step S4). In the example in FIG. 17, the optimum projection position is identified as a position of 0.5 (mm) to the right, for example.

The remainder of the configuration, operations, and effects may be substantially similar to those of the eyeball detection unit and the image display apparatus according to the foregoing first or second embodiment.

5. Fifth Embodiment

Next, an eyeball detection unit and an image display apparatus according to a fifth embodiment of the present disclosure will be described. It is to be noted that, in the following, components substantially the same as those of the eyeball detection unit and the image display apparatus according to any one of the foregoing first to fourth embodiments are denoted with the same reference numerals, and the description thereof is omitted where appropriate.

(Configuration and Operation of Eyeball Detection Unit)

FIGS. 18 to 20 each illustrate a configuration example of an eyeball detection unit 400D according to the fifth embodiment. Note that FIG. 18 illustrates the configuration example in a case where the state of the eyeball 200 is changed from the forward looking state and also a projection angle θ of the illumination light L11 is set to 0° (θ(0°)). FIG. 19 illustrates the configuration example in a case where the state of the eyeball 200 is changed from the forward looking state and also the projection angle θ of the illumination light L11 is moved in a + direction (θ (+)). FIG. 20 illustrates a configuration example in a case where the state of the eyeball 200 is changed from the forward looking state and also the projection angle θ of the illumination light L11 is moved in a − direction (θ(−)).

Relative to the configuration of the eyeball detection unit 400 according to the foregoing first embodiment, the eyeball detection unit 400D further includes a light beam angle controller 453. On the basis of an instruction from the detection controller 450, the light beam angle controller 453 changes the projection angle θ of the illumination light L11 with respect to the reference optical axis Z1 while the illumination light L11 is projected at a same projection position toward the cornea 203.

The detection controller 450 calculates the positional offset of the cornea position with respect to the reference optical axis Z1 on the basis of a change in a detected value by the detector 430 resulting from the projection angle θ of the illumination light L11 being changed by the light beam angle controller 453.

In each of FIGS. 18 to 20, a value of a detected light amount that is detected as a detected value is illustrated together with an example of the detected image 460 by the detector 430. As illustrated in FIGS. 18 to 20, changing the projection angle θ causes a change in the value of a light amount to be detected by the detector 430. The change in the value of the light amount varies depending on the angle of rotation of the eyeball 200, that is, depending on the cornea position. It is therefore possible to calculate the positional offset of the cornea position with respect to the reference optical axis Z1 on the basis of a change in the detected value by the detector 430 resulting from a change in the projection angle θ.

In the eyeball detection unit 400D according to the fifth embodiment, the detector 430 may not include divided detection regions because a light amount is detected as a detected value by the detector 430.

(Configuration and Operation of Image Display Apparatus)

FIGS. 21 and 22 each illustrate a configuration example of an image display apparatus 1C according to the fifth embodiment. FIG. 21 illustrates the configuration example of the image display apparatus 1C together with an optical path of the image light L0. FIG. 22 illustrates the configuration example of the image display apparatus 1C together with an optical path at the time of pupil position detection in the case where the eyeball 200 is in the forward looking state.

The image display apparatus 1C includes an image display system including the image light formation unit 100 (see FIG. 21), and a detection system that detects the pupil position of the viewer (see FIG. 22), substantially similarly to the configuration of the image display apparatus 1 according to the foregoing first embodiment.

In the image display apparatus 1C, the detection system has a configuration corresponding to the eyeball detection unit 400D described above.

The configuration of the image display system in the image display apparatus 1C includes components substantially similar to those of the configuration of the image display apparatus 1 according to the foregoing first embodiment. That is, the image display apparatus 1C includes, as the components of the image display system, the image light formation unit 100, the first reflective device 11, the second reflective device 12, the condensing optical system 20, the half mirror 21, and the collimator lens 104.

In the image display apparatus 1C, the detection system includes, as the components of the detection system, the detection device 31, the imaging lens 32, the wavelength cut filter 33, the illumination light source 34, and the detection controller 450, substantially similarly to the image display apparatus 1 according to the foregoing first embodiment.

The image display apparatus 1C further includes, as the components of the detection system, a fourth reflective device 14, an aperture 35, and the light beam angle controller 453. The aperture 35 is provided to cut unnecessary light having an offset centroid and included in the reflected light L12 entering the detection device 31.

In the image display apparatus 1C, the detection system is provided with the fourth reflective device 14, instead of the third reflective device 13, relative to the configuration of the detection system in the image display apparatus 1 according to the foregoing the first embodiment. In the detection system in the image display apparatus 1C, the arrangement position of the illumination light source 34 is different from that in the configuration of the detection system in the image display apparatus 1 according to the foregoing first embodiment. In the image display apparatus 1C, the fourth reflective device 14 is disposed on an optical path between the drawing light source 102 and the total reflective mirror 103 in the image light formation unit 100. The fourth reflective device 14 is a half mirror, and reflects the illumination light L11 emitted from the illumination light source 34 to cause the reflected light to enter the total reflective mirror 103. A subsequent optical path of the illumination light L11 to the eyeball 200 is similar to the that in the image display system. Further, the fourth reflective device 14 allows light from the drawing light source 102 to pass through.

On the basis of an instruction from the detection controller 450, the light beam angle controller 453 changes the projection angle $\theta$ of the illumination light L11 to the cornea 203 by controlling an angle of the scanning mirror 101, for example.

FIGS. 23 and 24 illustrate examples of detected images and detected light amounts at the time of pupil position detection in the image display apparatus 1C. FIG. 23 illustrates an example of the detected images and the detected light amounts in a case where the projection angle $\theta$ of the illumination light L11 is changed in the image display apparatus 1C while the eyeball 200 is in the forward looking state. FIG. 24 illustrates an example of the detected images and the detected light amounts in a case where the projection angle $\theta$ of the illumination light L11 is changed in the image display apparatus 1C, with the state of the eyeball 200 being changed from the forward looking state.

As illustrated in FIGS. 23 and 24, in the image display apparatus 1C, changing the projection angle $\theta$ of the illumination light L11 causes a change in the value of a light amount to be detected by the detection device 31. The change in the value of the light amount varies depending on the angle of rotation of the eyeball 200, that is, depending on the cornea position. It is therefore possible to calculate the positional offset of the cornea position with respect to the reference optical axis Z1 on the basis of a change in the detected value by the detection device 31 resulting from a change in the projection angle $\theta$.

The remainder of the configuration, operations, and effects may be substantially similar to those of the eyeball detection unit and the image display apparatus according to the foregoing first embodiment.

6. Sixth Embodiment

Next, an eyeball detection unit and an image display apparatus according to a sixth embodiment of the present disclosure will be described. It is to be noted that, in the following, components substantially the same as those of the eyeball detection unit and the image display apparatus according to any one of the foregoing first to fifth embodiments are denoted with the same reference numerals, and the description thereof is omitted where appropriate.

(Configuration and Operation of Eyeball Detection Unit)

FIG. 25 illustrates a configuration example of an eyeball detection unit 400E according to the sixth embodiment. FIG. 25 illustrates the configuration example of the eyeball detection unit 400E in an example case where the state of the eyeball 200 is changed from the forward looking state.

Relative to the configuration of the eyeball detection unit 400 according to the foregoing first embodiment, the eyeball detection unit 400E further includes a position controller 454.

On the basis of an instruction from the detection controller 450, the position controller 454 causes the projection position of the illumination light L11 to the cornea 203 to move with respect to the reference optical axis Z1, and causes the detection position of the light intensity by the detector 430 to move.

In the eyeball detection unit 400E, the detection controller 450 instructs the position controller 454 to cause the projection position of the illumination light L11 and the detection position to move to reduce the centroid offset in the angular direction with respect to the reference optical axis Z1.

Further, the detection controller 450 calculates the positional offset of the cornea position on the basis of the amount of movement of the projection position of the illumination light L11 and the amount of movement of the detection position.

(Configuration and Operation of Image Display Apparatus)

FIGS. 26 to 29 each illustrate a configuration example of an image display apparatus 1D according to the sixth embodiment. FIG. 26 illustrates the configuration example of the image display apparatus 1D together with an optical path of the image light L0. FIG. 27 illustrates the configuration example of the image display apparatus 1D together with an optical path at the time of pupil position detection in the case where the eyeball 200 is in the forward looking state. FIG. 28 illustrates the configuration example of the image display apparatus 1D together with an optical path at the time of pupil position detection in the case where the state of the eyeball 200 is changed from the forward looking state. FIG. 29 illustrates the configuration example of the image display apparatus 1D together with an optical path at the time of pupil position detection in the case where the state of the eyeball 200 is changed from the forward looking state and also the projection position of the illumination light L11 and the detection position are caused to move.

The image display apparatus 1D includes an image display system including the image light formation unit 100 (see FIG. 26), and a detection system that detects the pupil position of the viewer (see FIGS. 27 to 29), substantially similarly to the configuration of the image display apparatus 1 according to the foregoing first embodiment.

In the image display apparatus 1D, the detection system has a configuration corresponding to the eyeball detection unit 400E described above.

The configuration of the image display system in the image display apparatus 1D includes components substantially similar to those of the configuration of the image display apparatus 1 according to the foregoing first embodiment. That is, the image display apparatus 1D includes, as the components of the image display system, the image light formation unit 100, the first reflective device 11, the second reflective device 12, the condensing optical system 20, the half mirror 21, and the collimator lens 104.

In the image display apparatus 1D, the detection system includes, as the components of the detection system, the third reflective device 13, the detection device 31, the imaging lens 32, the wavelength cut filter 33, the illumination light source 34, and the detection controller 450, substantially similarly to the image display apparatus 1 according to the foregoing first embodiment.

The image display apparatus 1D further includes, as the components of the detection system, the fourth reflective device 14 and the position controller 454.

In the detection system in the image display apparatus 1D, the arrangement position of the illumination light source 34 and arrangement positions of the detection device 31, the imaging lens 32, and the wavelength cut filter 33 are different from those in the configuration of the detection system in the image display apparatus 1 according to the foregoing first embodiment. In the image display apparatus 1D, the fourth reflective device 14 is disposed on an optical path between the drawing light source 102 and the total reflective mirror 103 in the image light formation unit 100. The fourth reflective device 14 is a half mirror, and reflects the illumination light L11 emitted from the illumination light source 34 to cause the reflected light to enter the total reflective mirror 103. A subsequent optical path of the illumination light L11 to the eyeball 200 is similar to that in the image display system. Further, the fourth reflective device 14 allows light from the drawing light source 102 to pass through.

In the image display apparatus 1D, the reflected light L12 from the cornea 203 travels backward on the optical path of the image light L0, is reflected by the third reflective device 13, passes through the wavelength cut filter 33 and the imaging lens 32, and enters the detection device 31.

In the image display apparatus 1D, as an operation of the detection system, the detection controller 450 instructs, on the basis of the detected value by the detection device 31, the position controller 454 to cause the projection position of the illumination light L11 and the detection position to move to reduce the centroid offset in the angular direction of the light intensity of the reflected light L12 from the cornea 203 with respect to the reference optical axis Z1. On the basis of the instruction from the detection controller 450, the position controller 454 controls, for example, the disposition angle of the second reflective device 12 to thereby cause the projection position of the illumination light L11 to the cornea 203 and the detection position to move. As a result, it is possible to cause the projection position of the illumination light L11 and the convergence position of the image light L0 to move to appropriate positions.

The remainder of the configuration, operations, and effects may be substantially similar to those of the eyeball detection unit and the image display apparatus according to the foregoing first embodiment.

7. Other Embodiments

A technique according to the present disclosure is not limited to the description of each of the above embodiments, and may be modified in a variety of ways.

For example, the foregoing respective embodiments illustrate an example where the eyeball detection unit of the present disclosure is applied to an image display apparatus; however, the eyeball detection unit of the present disclosure is also applicable to apparatuses other than image display apparatuses.

For example, the present technology may be configured as follows.

According to the present technology with the following configuration, a centroid offset in the angular direction of the light intensity of the reflected light from the cornea with respect to the reference optical axis is identified on the basis of a detected value of the light intensity of the reflected light from the cornea, and thereafter a positional offset of the cornea position with respect to the reference optical axis is calculated. This makes it possible to perform pupil position detection with less arithmetic load and power consumption.

(1)
An eyeball detection unit including:
an irradiator that projects substantially parallel illumination light toward a cornea of an eyeball;
a detector that detects light intensity of reflected light from the cornea; and
a detection controller that identifies a centroid offset in an angular direction of the light intensity of the reflected light from the cornea with respect to a reference optical axis on the basis of a detected value by the detector, and thereafter calculates a positional offset of a cornea position with respect to the reference optical axis.

(2)
The eyeball detection unit according to (1), further including a light beam position controller that causes, on the basis of an instruction from the detection controller, a projection position of the illumination light to the cornea to move with respect to the reference optical axis,
in which the detection controller instructs the light beam position controller to cause the projection position of the illumination light to move to reduce the centroid offset in the angular direction with respect to the reference optical axis, and calculates the positional offset of the cornea position on the basis of an amount of movement of the projection position of the illumination light.

(3)
The eyeball detection unit according to (2), further including a detection position controller that causes, on the basis of an instruction from the detection controller, a detection position of the light intensity by the detector to move,
in which the detection controller instructs the light beam position controller to cause the projection position of the illumination light to move to reduce the centroid offset in the angular direction with respect to the reference optical axis, instructs the detection position controller to cause the detection position to move, and calculates the positional offset of the cornea position on the basis of the amount of movement of the projection position of the illumination light and an amount of movement of the detection position.

(4)
The eyeball detection unit according to (1), further including a light beam position controller that causes, on the basis of an instruction from the detection controller, a projection position of the illumination light to the cornea to move with respect to the reference optical axis,
in which the detection controller
stores a relationship table of a reference value of the centroid offset associated with an amount of movement of the projection position of the illumination light and the positional offset of the cornea position, references the relationship table and calculates the positional offset of the cornea position on the basis of the amount of movement of the projection position of the illumination light and the centroid offset identified on the basis of the detected value by the detector, and thereafter calculates an optimum projection position for the calculated positional offset of the cornea position by referencing the relationship table, and instructs the light beam position controller to cause the projection position of the irradiation light to move to approach the calculated optimum projection position.

(5)

The eyeball detection unit according to (1), further including a light beam angle controller that changes a projection angle of the illumination light with respect to the reference optical axis while the illumination light is projected at a same projection position toward the cornea, in which the detection controller calculates the positional offset of the cornea position with respect to the reference optical axis on the basis of a change in the detected value by the detector resulting from the projection angle of the illumination light being changed by the light beam angle controller.

(6)

The eyeball detection unit according to any one of (1) to (4), in which the detector includes a plurality of divided detection regions, and the detection controller identifies the centroid offset in the angular direction of the light intensity of the reflected light from the cornea with respect to the reference optical axis on the basis of a detected value of an intensity of received light in each of the plurality of divided detection regions.

(7)

The eyeball detection unit according to any one of (1) to (6), further including a condensing and detection optical system that condenses the reflected light from the cornea toward the detector, in which the detector is disposed at a position off a focal position on a detector side of the condensing and detection optical system.

(8)

The eyeball detection unit according to (1), further including a position controller that, on the basis of an instruction from the detection controller, causes a projection position of the illumination light to the cornea to move with respect to the reference optical axis, and also causes a detection position of the light intensity by the detector to move, in which the detection controller instructs the position controller to cause the projection position of the illumination light and the detection position to move to reduce the centroid offset in the angular direction with respect to the reference optical axis, and calculates the positional offset of the cornea position on the basis of an amount of movement of the projection position of the illumination light and an amount of movement of the detection position.

(9)

The eyeball detection unit according to any one of (1) to (8), in which the reference optical axis is a straight line including a center of curvature of the cornea in a case where the eyeball is in a forward looking state and a center of rotation of the eyeball.

(10)

The eyeball detection unit according to any one of (1) to (9), in which the detection controller detects, as the positional offset of the cornea position, a positional offset of a center of curvature of the cornea with respect to the reference optical axis.

(11)

An image display apparatus including:

an image light formation unit that outputs image light;

a condensing optical system that causes the image light to converge toward a cornea of a viewer; and an eyeball detection unit, the eyeball detection unit including an irradiator that projects substantially parallel illumination light toward the cornea of the eyeball, with a projection position thereof lying at substantially a same position as a convergence position of the image light, a detector that detects light intensity of reflected light from the cornea, and a detection controller that identifies a centroid offset in an angular direction of the light intensity of the reflected light from the cornea with respect to a reference optical axis on the basis of a detected value by the detector, and thereafter calculates a positional offset of a cornea position with respect to the reference optical axis.

(12)

The image display apparatus according to (11), further including a light beam position controller that causes, on the basis of the positional offset of the cornea position detected by the eyeball detection unit, the projection position of the illumination light and the convergence position of the image light to move.

This application claims priority from Japanese Patent Application No. 2018-113779 filed with the Japan Patent Office on Jun. 14, 2018, the entire contents of which are incorporated herein by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. An eyeball detection unit, comprising:
    an irradiator configured to project illumination light toward a cornea of an eyeball;
    a detector configured to detect light intensity of reflected light from the cornea, wherein the reflected light is associated with the projected illumination light; and
    a detection controller configured to:
        identify a centroid offset in an angular direction of the light intensity of the reflected light from the cornea with respect to a reference optical axis, based on the detected light intensity of the reflected light;
        control a light beam position controller to move a projection position of the illumination light to reduce the identified centroid offset in the angular direction with respect to the reference optical axis;
        control a detection position controller to move a detection position of the light intensity of the reflected light based on movement of the projection position of the illumination light; and
        calculate a positional offset of a position of the cornea with respect to the reference optical axis, based on an amount of the movement of the projection position of the illumination light and an amount of movement of the detection position of the light intensity of the reflected light.

2. The eyeball detection unit according to claim 1, further comprising a light beam angle controller, wherein the detection controller is further configured to:

control the light beam angle controller to change a projection angle of the illumination light with respect to the reference optical axis; and
wherein the positional offset of the position of the cornea is further calculated with respect to the reference optical axis based on a change in a value of the detected light intensity of the reflected light, and
wherein the value of the detected light intensity of the reflected light is changed based on the change in the projection angle of the illumination light.

3. The eyeball detection unit according to claim 1, wherein
the detection controller is further configured to identify the centroid offset in the angular direction of the light intensity of the reflected light with respect to the reference optical axis, based on the detected light intensity of the reflected light in each of a plurality of detection regions,
wherein the detector includes the plurality of detection regions.

4. The eyeball detection unit according to claim 1, further comprising a condensing and detection optical system configured to condense the reflected light from the cornea toward the detector,
wherein the detector is at a position different from a focal position on a detector side of the condensing and detection optical system.

5. The eyeball detection unit according to claim 1, wherein the reference optical axis is a straight line including a center of curvature of the cornea, based on a forward looking state of the eyeball, and a center of rotation of the eyeball.

6. The eyeball detection unit according to claim 1, wherein the detection controller is further configured to detect, as the positional offset of the position of the cornea, a positional offset of a center of curvature of the cornea with respect to the reference optical axis.

7. An image display apparatus, comprising:
an image light formation unit configured to output image light;
a condensing optical system configured to control the image light to converge toward a cornea of a viewer; and
an eyeball detection unit, wherein the eyeball detection unit includes:
an irradiator configured to project illumination light toward the cornea of an eyeball of the viewer, wherein a projection position of the illumination light is same as a convergence position of the image light;
a detector configured to detect light intensity of reflected light from the cornea, wherein the reflected light is associated with the projected illumination light; and
a detection controller configured to:
identify a centroid offset in an angular direction of the light intensity of the reflected light from the cornea with respect to a reference optical axis, based on the detected light intensity of the reflected light;
control a light beam position controller to move the projection position of the illumination light to reduce the identified centroid offset in the angular direction with respect to the reference optical axis;
control a detection position controller to move a detection position of the light intensity of the reflected light based on movement of the projection position of the illumination light; and
calculate a positional offset of a position of the cornea with respect to the reference optical axis, based on an amount of the movement of the projection position of the illumination light and an amount of movement of the detection position of the light intensity of the reflected light.

8. The image display apparatus according to claim 7, wherein the detection controller is further configured to control the light beam position controller, based on the calculated positional offset of the position of the cornea, to move the projection position of the illumination light and the convergence position of the image light.

9. An eyeball detection unit, comprising:
an irradiator configured to project illumination light toward a cornea of an eyeball;
a detector configured to detect light intensity of reflected light from the cornea, wherein the reflected light is associated with the projected illumination light; and
a detection controller configured to:
control a light beam position controller to move a projection position of the illumination light with respect to a reference optical axis;
identify a centroid offset in an angular direction of the light intensity of the reflected light from the cornea with respect to the reference optical axis, based on:
the detected light intensity of the reflected light, and
movement of the projection position of the illumination light;
store a relationship table that includes a relationship between a reference value of the identified centroid offset associated with an amount of the movement of the projection position of the illumination light and a positional offset of a position of the cornea corresponding to the reference value of the identified centroid offset;
calculate the positional offset of the position of the cornea corresponding to the amount of the movement of the projection position of the illumination light and the identified centroid offset based on the stored relationship table;
calculate an optimum projection position for the calculated positional offset of the position of the cornea based on the relationship table; and
control the light beam position controller to move the projection position of the illumination light that approaches the calculated optimum projection position.

* * * * *